United States Patent [19]

Hachiya

[11] Patent Number: 4,954,600
[45] Date of Patent: Sep. 4, 1990

[54] FERROELECTRIC LIQUID-CRYSTALLINE POLYMER AND EPOXIDE USABLE TO PREPARATION OF THE FERROELECTRIC LIQUID-CRYSTALLINE POLYMER

[75] Inventor: Satoshi Hachiya, Chiba, Japan

[73] Assignee: Idemitsu Kosan Co., Ltd., Tokyo, Japan

[21] Appl. No.: 367,252

[22] Filed: Jun. 16, 1989

[30] Foreign Application Priority Data

Jun. 27, 1988 [JP] Japan ............................. 63-156789
Apr. 27, 1989 [JP] Japan ............................. 1-105788

[51] Int. Cl.$^5$ .................... C08G 65/22; C09K 19/52
[52] U.S. Cl. .................................... 528/89; 528/100; 252/299.01; 252/299.66; 350/350 R; 549/560
[58] Field of Search ........................ 528/98, 100; 252/299.01, 299.66; 549/560

[56] References Cited

U.S. PATENT DOCUMENTS

| | | | |
|---|---|---|---|
| 3,408,407 | 10/1968 | Cotter et al. ............... | 528/98 X |
| 4,665,150 | 5/1987 | Tesch et al. ................ | 528/98 |
| 4,746,718 | 5/1988 | Gardner et al. ............. | 528/98 |
| 4,762,901 | 8/1988 | Dhein et al. ................ | 528/100 X |
| 4,764,581 | 8/1988 | Müller et al. ............... | 528/100 |
| 4,877,858 | 10/1989 | Machiya et al. ............ | 528/100 |

Primary Examiner—Earl Nielsen
Attorney, Agent, or Firm—Antonelli, Terry, Stout & Kraus

[57] ABSTRACT

A ferroelectric liquid-crystalline polymer consisting essentially of at least one repeating unit represented by the following general formula:

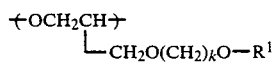

wherein
k is an integer having a value of 2 to 30;
$R^1$ is

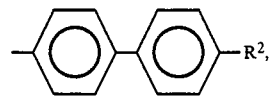

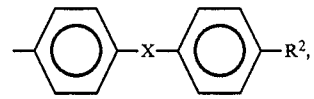

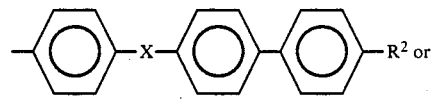

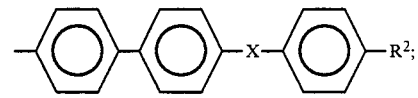

X is —COO— or —OCO—; and
$R^2$ is —COOR$^3$, —OCOR$^3$ or —OR$^3$;
wherein $R^3$ is

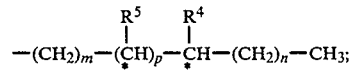

wherein
each of $R^4$ and $R^5$ is independently —CH$_3$, a halogen atom or —CN;
each of m and n is independently an integer having a value of 0 to 10, with the proviso that when $R^4$ is —CH$_3$, n is not an integer having a value of 0;
p is an integer having a value of 0 or 1; and
C marked with * is an asymmetric carbon atom.

6 Claims, 23 Drawing Sheets

FERROELECTRIC LIQUID-CRYSTALLINE POLYMER AND EPOXIDE USABLE TO PREPARATION OF THE FERROELECTRIC LIQUID-CRYSTALLINE POLYMER

BACKGROUND OF THE INVENTION (a) Industrial Field of the Invention

The present invention relates to novel ferroelectric liquid-crystalline polymers and to epoxides that are usable as monomers to preparation of the ferroelectric liquid-crystalline polymer. More particularly, the present invention relates to ferroelectric liquid-crystalline polymers which not only exhibit ferroelectricity even at temperatures around room temperature, but also have such a high speed of response to external factors that they can be used for displaying moving pictures, and are able to be advantageously used as display devices for large displays or curved displays. Such liquid-crystalline polymers are useful in optoelectronics fields as various electronic optical devices, particularly, as display devices for desk calculators, clocks and watches, etc., electronic optical shutters, electronic optical diaphragms, optical modulators, optical-path transfer switches in optical communication systems, memories, liquid crystal printer heads, variable-focal-length lenses, and so forth.

(2) Description of the Related Art

Display devices employing low molecular weight liquid-crystalline compounds have been widely used for digital display in desk calculators, clocks and watches, etc. In these fields of utilization, conventional low molecular weight liquid crystal compounds are sandwiched between a couple of glass substrates, the space between the glass substrates being adjusted with a precision to an extent of micrometers. However, such a precise adjustment of the space has actually been impossible in large displays or curved displays.

In order to solve the problem, it has been attempted to develop polymeric liquid crystals so as to make it possible to mold liquid crystals themselves (cf., J. Polym. Sci., Polym. Lett., Ed. 13, 243 (1975), Polym. Bull., 6, 309 (1982), Japanese Patent Application Laid-open No. 55-21479, etc.).

Nevertheless, the liquid crystal polymers resulting from the above attempts have an disadvantage in that the polymers do not exhibit any liquid crystal properties unless they are heated at temperatures between their glass transition temperatures and their clearing points.

In Japanese Patent Application Laid-open No. 63-99204, disclosed is the synthesis of polyacrylate ferroelectric liquid-crystalline polymers that are confirmed to outperform the above-described liquid-crystalline polymers. However, there is yet room for improvement in the response speed and the utilizable temperature range of the polyacrylate ferroelectric liquid-crystalline polymers.

SUMMARY OF THE INVENTION

An object of the present invention is to provide liquid-crystalline polymers which exhibit ferroelectricity in a wide range of temperature including room temperature and further respond to external factors, particularly to electric field at a high speed in a wide range of temperature. That is, an object of the present invention is to provide novel ferroelectric liquid-crystalline polymers which when they are used as display devices, make it possible to display moving pictures and to produce large displays or curved displays.

Another object of the present invention is to provide epoxides which are usable as the monomers to the production of the ferroelectric liquid-crystalline polymers of the present invention.

We found as the result of researches that polyether-type polymers having specific structure exhibit ferroelectricity at or around room temperature and, eventually, completed the present invention.

According to the present invention, there is provided a ferroelectric liquid-crystalline polymer consisting essentially of at least one repeating unit represented by the following general formula:

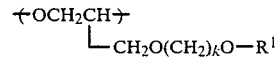

wherein
k is an integer having a value of 2 to 30;
$R^1$ is

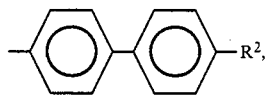

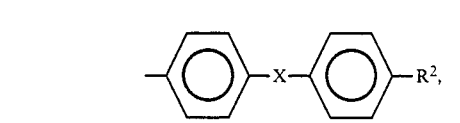

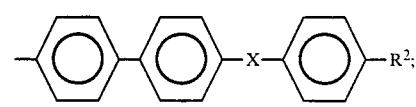

X is —COO— or —OCO—; and
$R^2$ is —COOR$^3$, —OCOR$^3$ or —OR$^3$;
wherein $R^3$ is

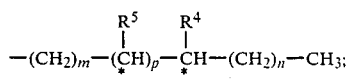

wherein
each of $R^4$ and $R^5$ is independently —CH$_3$, a halogen atom or —CN;
each of m and n is independently an integer having a value of 0 to 10, with the proviso that when $R^4$ is —CH$_3$, n is not an integer having a value of 0;
p is an integer having a value of 0 or 1; and
C marked with * is an asymmetric carbon atom.

According to the present invention, there is also provided an epoxide having the structure represented by the following general formula:

wherein k is an integer having a value of 2 to 30;
R¹ is

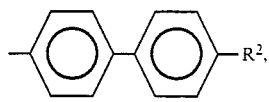

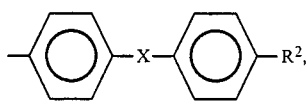

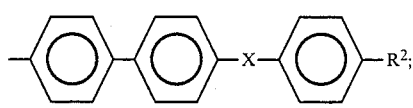

X is —COO— or —OCO—; and
R² is —COOR³, —OCOR³ or —OR³;
wherein R³ is

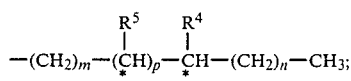

wherein
each of R⁴ and R⁵ is independently —CH₃, a halogen atom or —CN;
each of m and n is independently an integer having a value of 0 to 10, with the proviso that when R⁴ is —CH₃, n is not an integer having a value of 0;
p is an integer having a value of 0 or 1; and
C marked with * is an asymmetric carbon atom.

DESCRIPTION OF THE PREFERRED EMBODIMENTS

Figure 1:
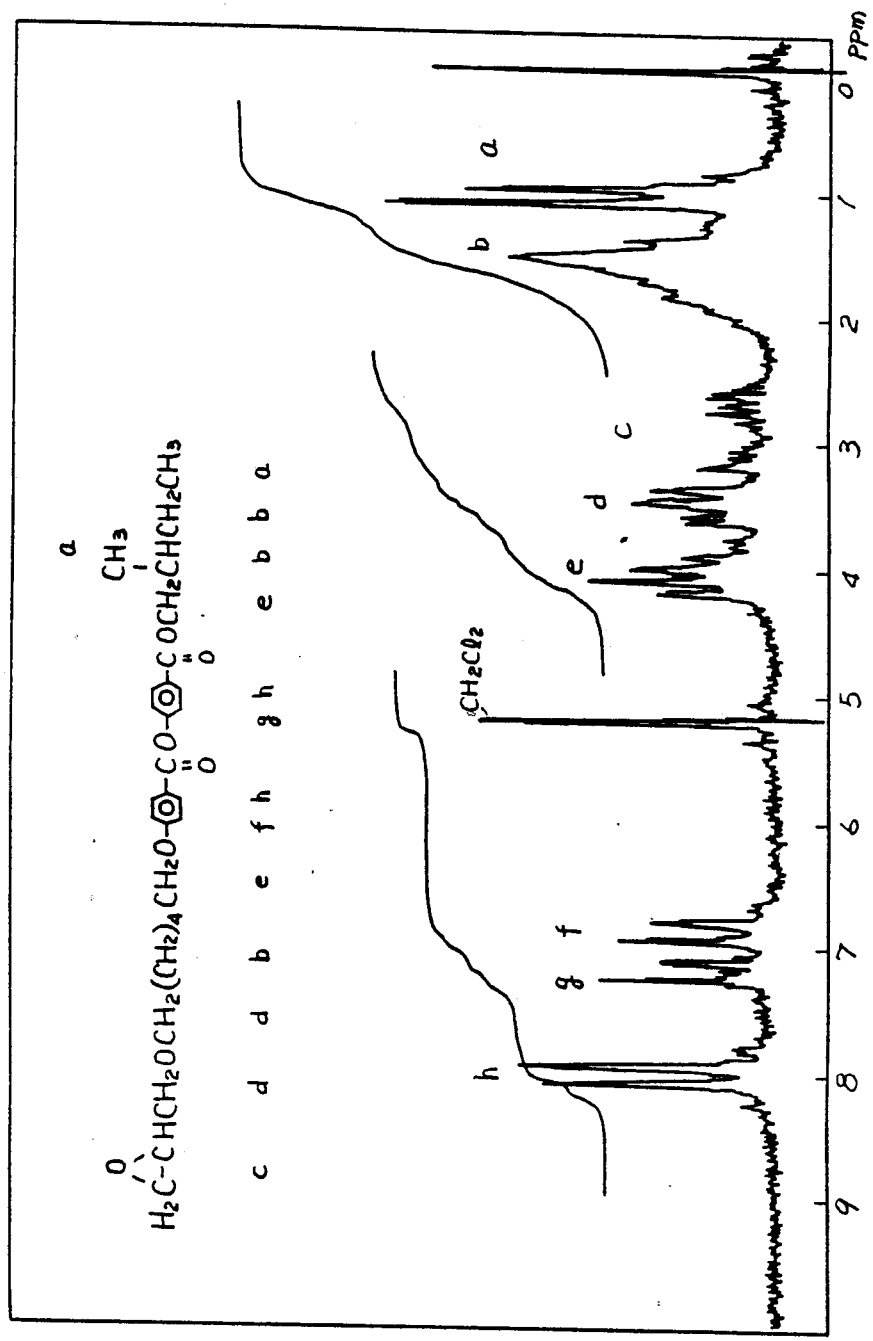
FIG. 1 is a chart of NMR spectrum of the epoxide obtained in Example 1.

The preferred liquid-crystalline polymers of the present invention are those having a number average molecular weight of 1,000 to 400,000. If the number average molecular weight is less than 1,000, the moldability of the polymers into films or coated films may be sometimes deteriorated. If it is more than 400,000, there may sometimes appear undesirable effects such as the lowered speed of response. The particularly preferred range of the number average molecular weight cannot be uniformly limited because it varies depending on the kind of R¹, the numerical value of "k", the optical purity of R³, etc., but is generally from 1,000 to 200,000.

k is an integer having a value of 2 to 30, preferably 4 to 20. Each of m and n is independently an integer having a value of 0 to 10, preferably 0 to 6.

The general methods of preparing the liquid-crystalline polymers of the present invention are given as under.

For example, the liquid-crystalline polymers of the present invention may be prepared by using the epoxides of the present invention. That is, the liquid-crystalline polymers of the present invention may be prepared by polymerizing at least one monomer that is an epoxide represented by the following general formula:

wherein k, X, R¹, R², R³, R⁴, R⁵, m, m, and p are as defined above.

The epoxides that are the above monomers may be obtained by, for example, as follows.

(1) In a case where R¹ is

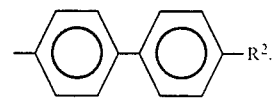

As shown in the following reaction formulas, an allyl alcohol is etherified with an α,ω-dihaloalkane (I) by dissolving them in a solvent, such as hexane, and then adding to the obtained solution a 50% aqueous sodium hydroxide solution and a phase-to-phase transferring catalyst, such as tetrabutylammonium bromide, to obtain an ω-haloalkyl allyl ether (II). Alternatively, an ω-haloalkyl allyl ether (II) is prepared by etherifying an allyl alcohol with an α,ω-dihaloalkane (I) by dissolving them in a solvent, such as tetrahydrofuran (THF), followed by adding sodium hydride. The obtained ω-haloalkyl allyl ether (II) and a compound (III) are reacted in an appropriate solvent, such as 2-butanone, in the presence of an alkali, such as potassium carbonate, to obtain an allyl ether compound (IV). Subsequently, the allyl ether compound (IV) is converted to the objective epoxide (V) with a peracid, such as m-chloroperbenzoic acid, in an appropriate solvent such as dichloromethane.

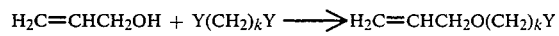

(I)  (II)

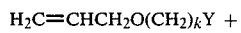

(II)

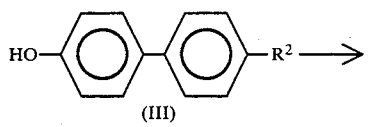

(III)

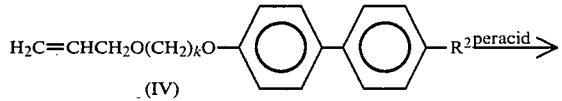

(IV)

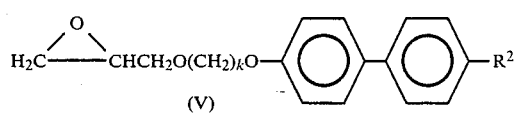

(V)

(In the above formulas, Y is a halogen.)

The preferred examples of the α,ω-dihaloalkane which may be used in the present invention include 1,4-dibromobutane, 1,6-dibromohexane, 1,8-dibromooctane, 1,10-diiododecane, 1,12-dibromododecane, and 1,14-dibromotetradecane.

The above compound (III),

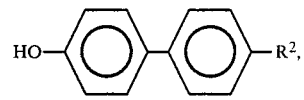

may be prepared as follows.

Synthesis of

As shown in the following reaction formula, the ester compound (VII) may be obtained by reacting 4'-hydroxybiphenyl-4-carboxylic acid with an optically active alcohol (VI) in an appropriate solvent, such as benzene, in the presence of an esterification catalyst, such as concentrated sulfuric acid or p-toluenesulfonic acid, at a desired temperature.

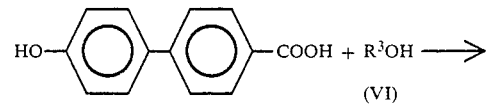

(VI)

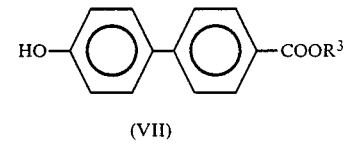

(VII)

Some illustrative examples of the optically active alcohol (VI) which may be used include (+)-2-methylbutanol, (−)-2-methylbutanol, (+)-2-chlorobutanol, (−)-2-chlorobutanol, (+)-2-methylpentanol, (−)-2-methylpentanol, (+)-3-methylpentanol, (−)-3-methylpentanol, (+)-4-methylhexanol, (−)-4-methylhexanol, (+)-2-chloropropanol, (−)-2-chloropropanol, (+)-1-methylheptanol, (−)-1-methylheptanol, (+)-6-methyloctanol, (−)-6-methyloctanol, (+)-2-cyanobutanol, (−)-2-cyanobutanol, (+)-2-butanol, (−)-2-butanol, (+)-2-pentanol, (−)-2-pentanol, (+)-2-octanol, (−)-2-octanol, (−)-2-fluorooctanol, (−)-2-fluorooctanol, (−)-2-fluorohexanol, (−)-2-fluorohexanol, (−)-2-flurononanol, (−)-2-flurononanol, (−)-2-chloro-3-methylpentanol, and (−)-2-chloro-3-methylpentanol.

The preferred are (−)-2-methylbutanol, (+)-2-butanol, (−)-2-pentanol, (−)-2-octanol, (−)-2-fluorooctanol, (−)-2-fluorohexanol, and (−)-2-chloro-3-methylpentanol.

Synthesis of

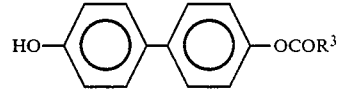

As shown in the following reaction formula, the ester compounds (IX) may be prepared by reacting biphenyl-4,4'-diol with an optically active carboxylic acid (VIII).

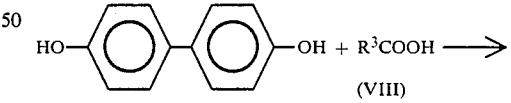

(VIII)

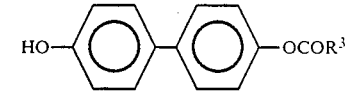

(IX)

Some illustrative examples of the optically active carboxylic acid (VIII) which may be used include (+)-2-methylbutanoic acid, (−)-2-methylbutanoic acid, (+)-2-chlorobutanoic acid, (−)-2-chlorobutanoic acid, (+)-2-methylpentanoic acid, (−)-2-methylpentanoic acid, (+)-3-methylpentanoic acid, (−)-3-methylpentanoic acid, (+)-4-methylhexanoic acid, (−)-4-methylhexanoic acid, (+)-2-chloropropanoic acid, (−)-2- chloropropanoic acid, (+)-6-methyloctanoic acid, (−)-6-methyloctanoic acid, (+)-2-cyanobutanoic acid, (−)-2-cyanobutanoic acid, (+)-2-fluorooctanoic acid, (−)-2-fluorooctanoic acid, (+)-2-chloro-3-methylpentanoic acid, and (−)-2-chloro-3-methylpentanoic acid.

Synthesis of

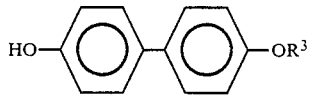

As shown in the following reaction formulas, the ether compounds (X) may be obtained by tosylating the above-described optically active alcohols (VI), followed by reacting the alcohols (VI) with biphenyl-4,4'-diol.

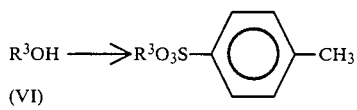

(VI)

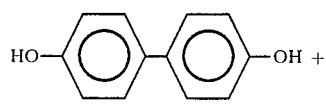

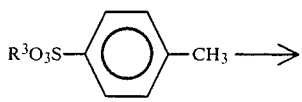

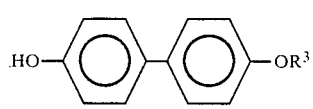

(2) In a case where $R^1$ is

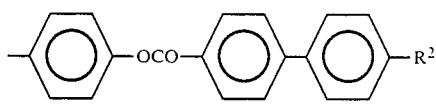

As shown in the following reaction formulas, an ω-haloalkyl allyl ether (II) is reacted with ethyl p-hydroxybenzoate in an appropriate solvent, such as acetone, in the presence of an alkali such as potassium carbonate, to obtain an ether compound. Subsequently, the ether compound is converted to a carboxylic acid compound by eliminating the group protecting the carboxyl group of the ether compound, using an aqueous potassium hydroxide solution, hydrochloric acid or the like. The carboxylic acid is then converted to an acid halide by adding a halogenation agent, such as thionyl chloride, and heating in a solvent, such as toluene. Then the acid halide and the above compound (III) are reacted in a solvent, such as toluene, in the presence of pyridine, to obtain an allyl ether compound (XI). The compound (XI) is subsequently converted to the objective epoxide (XII) using an peracid, such as m-chloroperbenzoic acid, in an appropriate solvent, such as dichloromethane.

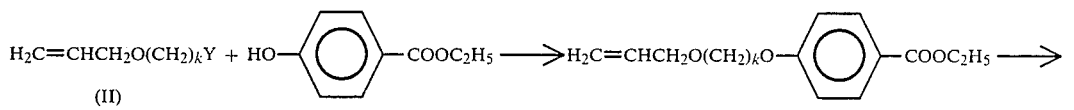

(II)

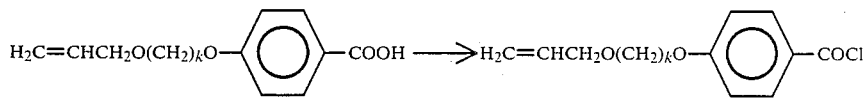

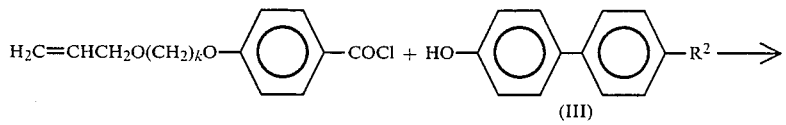

(III)

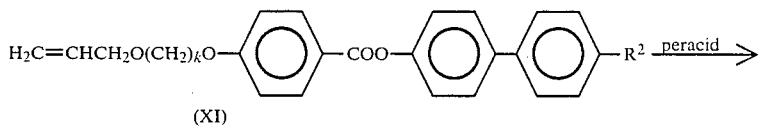

(XI)

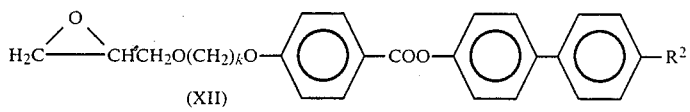

(XII)

(3) In a case where $R^1$ is

As shown in the following reaction formulas, an ω-haloalkyl allyl ether (II) is reacted with hydroquinone in the presence of an alkali, such as potassium carbonate, to obtain an ether compound (XIII).

A compound (XIV) is converted to an acid chloride with thionyl chloride, etc. The obtained acid chloride and the ether compound (XIII) are reacted in the presence of pyridine, to obtain an allyl ether compound (XV). Thereafter, conversion to epoxide is carried out in the same manner in (1), to obtain the objective epoxide (XVI).

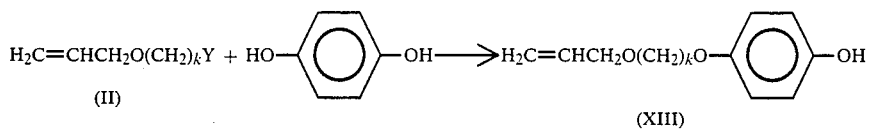
(II)                                                    (XIII)

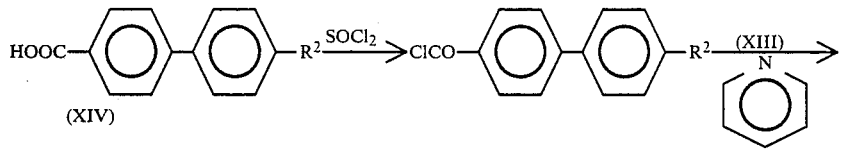
(XIV)

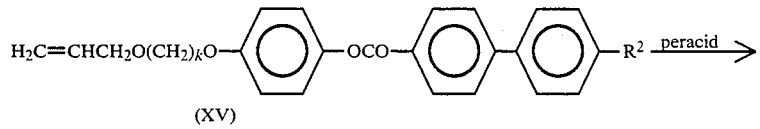
(XV)

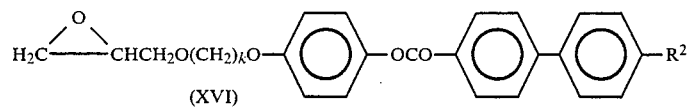
(XVI)

The above compounds (XIV),

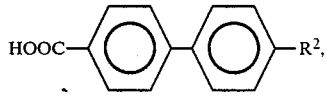

may be prepared as follows.

Synthesis of

The objective ester compounds (XVII) may be obtained by reacting an optically active alcohol (VI) with biphenyl-4,4'-dicarboxylic acid in a solvent, such as toluene, in the presence of an esterification catalyst.

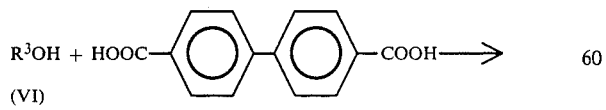

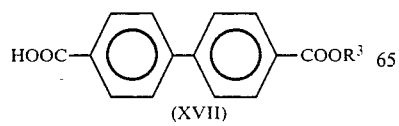
(XVII)

Synthesis of

The objective ester compounds (XVIII) may be obtained by converting an optically active carboxylic acid (VIII) to an acid chloride with thionyl chloride or the like, followed by reacting the acid chloride with 4'-hydroxybiphenyl-4-carboxylic acid, in the presence of pyridine.

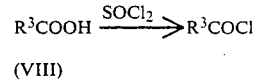
(VIII)

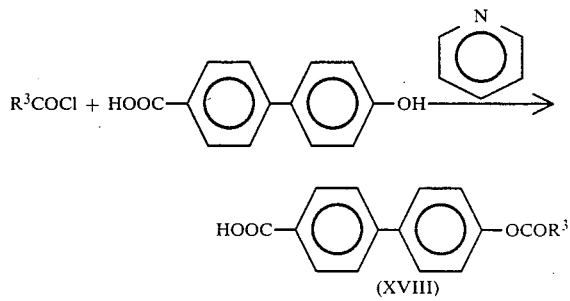
(XVIII)

Synthesis of

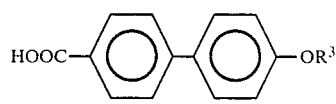

Ethyl 4'-hydroxybiphenyl-4-carboxylate and

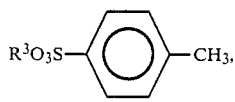

which is obtained by tosylating an optically active alcohol (VI), are reacted in the presence of potassium carbonate or the like, to obtain an ether compound. The ether compound is subjected to hydrolysis by reacting it with an aqueous alkali solution to eliminate the protecting group, to obtain the objective compound (XIX).

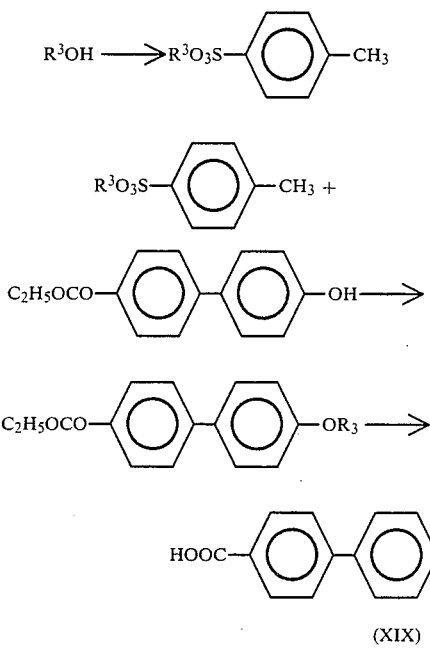

(XIX)

(4) In a case where $R^1$ is

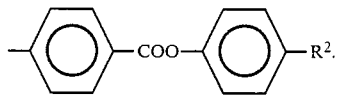

The objective epoxides (XXI) having the structure represented by the following general formula may be prepared by the same reactions in the synthesis of the epoxide wherein $R^1$ is

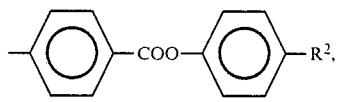

which is described in the above paragraph (2), with the exception that a compound (XX),

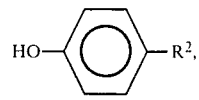

is used in place of the compounds (III),

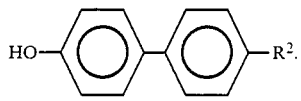

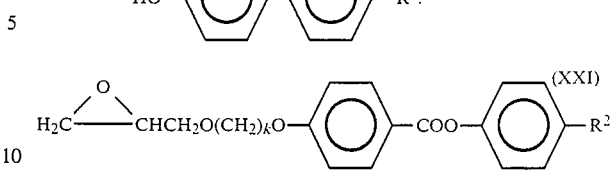

The compounds (XX) may be prepared as follows.

Synthesis of

HO—⟨○⟩—COOR³

The objective ester compounds (XXII) may be prepared by the same reactions in the synthesis of the compounds (VII) in (1) with the exception that p-hydroxybenzoic acid is used in place of 4'-hydroxybiphenyl-4-carboxylic acid.

Synthesis of

HO—⟨○⟩—OCOR³

The objective ester compounds (XXIII) may be prepared by the same reactions in the synthesis of the compounds (VIII) in (1) with the exception that hydroquinone is used in place a biphenyl-4,4'-diol.

Synthesis of

HO—⟨○⟩—OR³

The objective ether compounds (XXIV) may be prepared by the same reactions in the synthesis of the compounds (X) in (1) with the exception that hydroquinone is used in place of biphenyl-4,4'-diol.

(5) In a case where $R^1$ is

—⟨○⟩—OCO—⟨○⟩—R².

As shown in the following reaction formulas, the objective epoxides (XXVI) represented by the following general formula may be prepared by the same reactions in the synthesis of the epoxides wherein $R^1$ is

—⟨○⟩—OCO—⟨○⟩—⟨○⟩—R² in (3) with the exception that a compound (XXV),

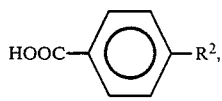

is used in place of the compounds (XIV),

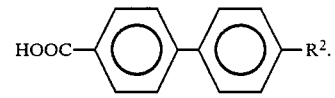

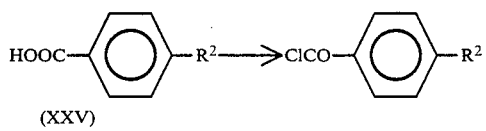
(XXV)

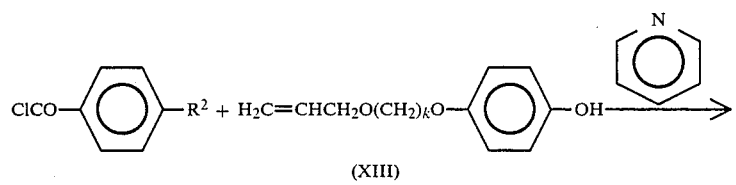
(XIII)

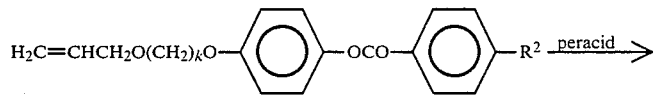

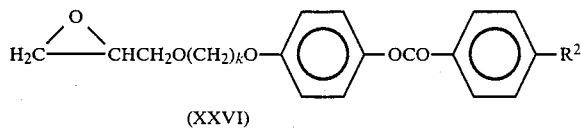
(XXVI)

The compounds (XXV) may be prepared as follows.

Synthesis of

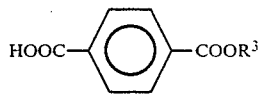

The objective ester compounds (XXVII) may be prepared by the same reactions in the synthesis of the compounds (XVII) in (3) with the exception that terephthalic acid is used in place of biphenyl-4,4'-dicarboxylic acid.

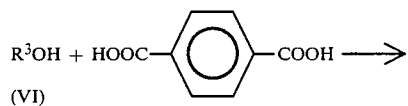
(VI)

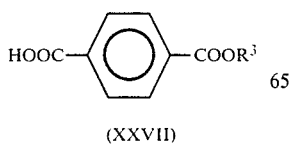
(XXVII)

Synthesis of

The objective ester compounds (XXVII) may be prepared by the same reactions in the synthesis of the compounds (XVIII) in (3) with the exception that p-hydroxybenzoic acid is used in place of 4'-hydroxybiphenyl-4-carboxylic acid.

$R^3COOH \longrightarrow R^3COCl$
(VIII)

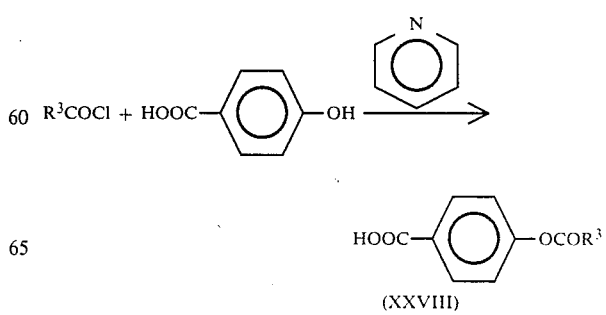

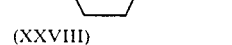
(XXVIII)

Synthesis of

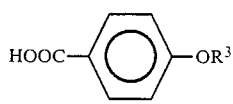

The objective ether compounds (XXIX) may be prepared by the same reactions in the synthesis of the compounds (XIV) in (3) with the exception that ethyl p-hydroxybenzoate is used in place of ethyl 4'-hydroxybiphenyl-4-carboxylate.

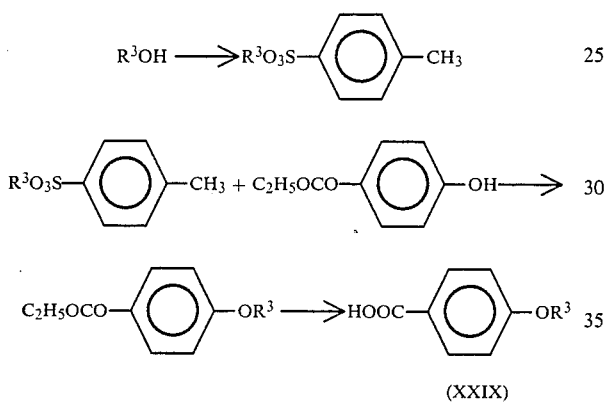

(XXIX)

(6) In a case where $R^1$ is

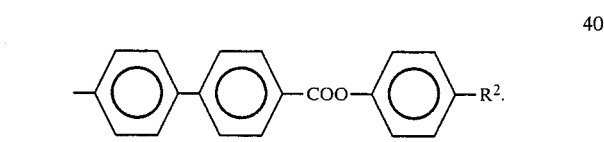

The objective epoxides represented by the following general formula (XXX) may be prepared by the same reactions in the synthesis of epoxides wherein $R^1$ is

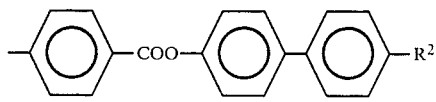

in (2) with the exception that ethyl 4'-hydroxybiphenyl-4-carboxylate is used in place of ethyl p-hydroxybenzoate, and the compounds (XX),

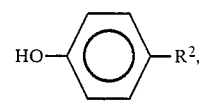

are used in place of the compounds (III),

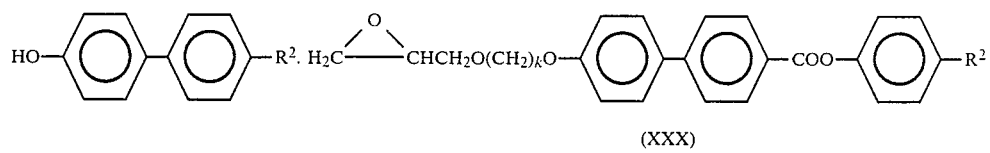

(XXX)

(7) In a case where $R^1$ is

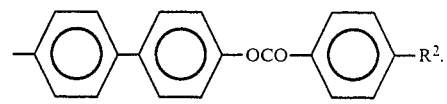

The objective epoxides (XXXI) represented by the following general formula may be prepared by the same reactions in the synthesis of the epoxides wherein $R^1$ is

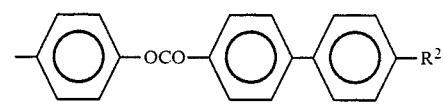

in (3) with the exception that biphenyl-4,4'-diol is used in place of hydroquinone, and the compounds (XXV),

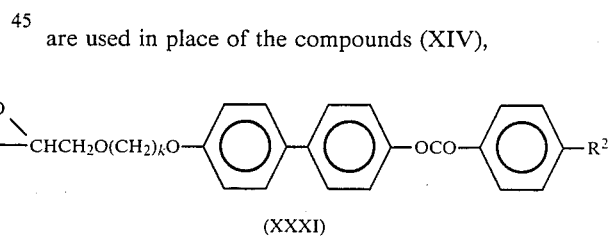

are used in place of the compounds (XIV),

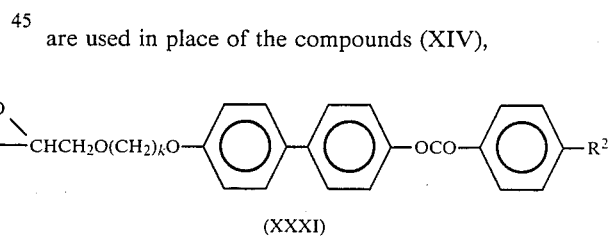

(XXXI)

Some illustrative examples of the epoxides, which are the monomers for the production of the polymers of the present invention, include those represented by the following formulas.

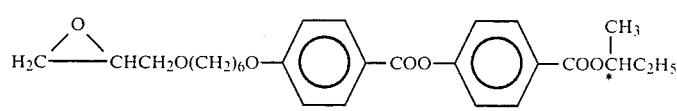

1.

-continued
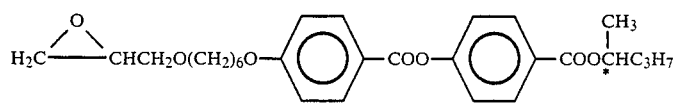 2.
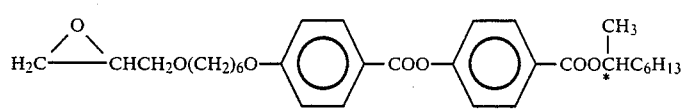 3.
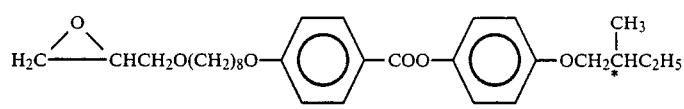 4.
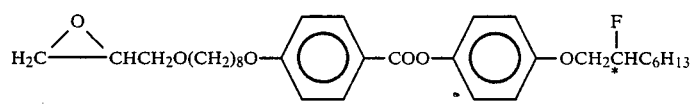 5.
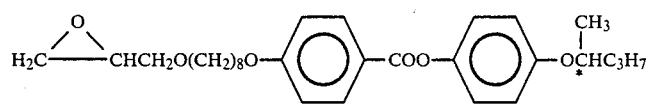 6.
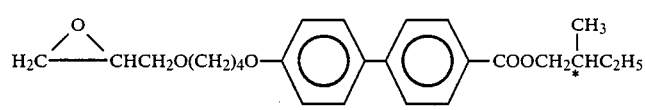 7.
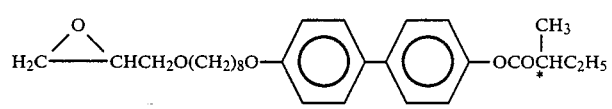 8.
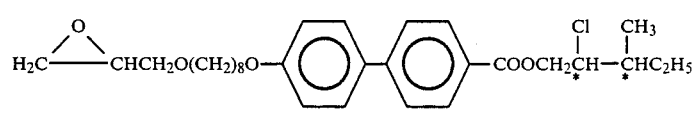 9.
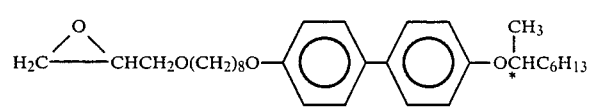 10.
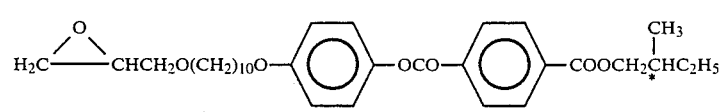 11.
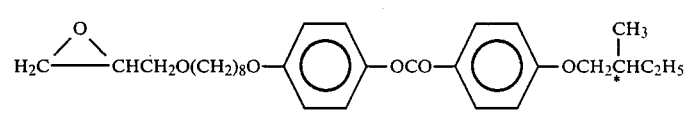 12.
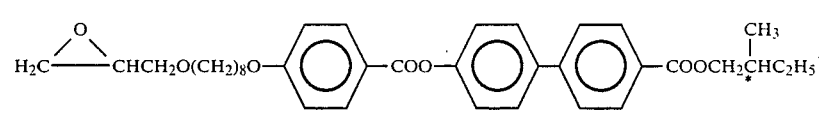 13.
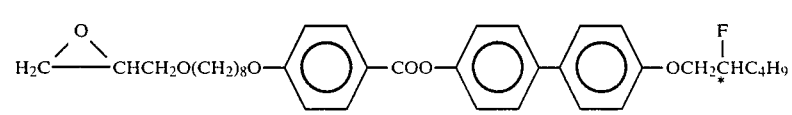 14.
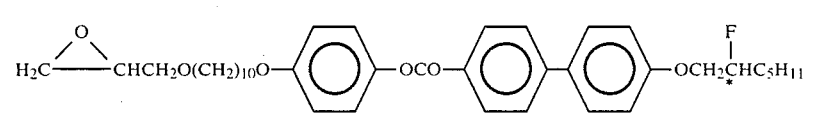 15.

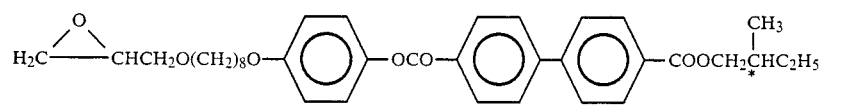 16.
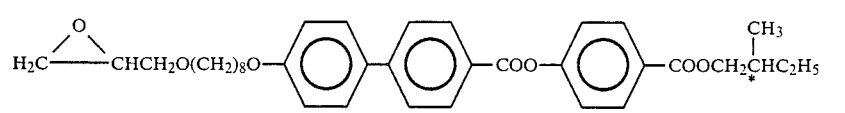 17.
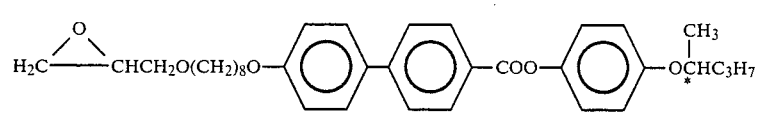 18.
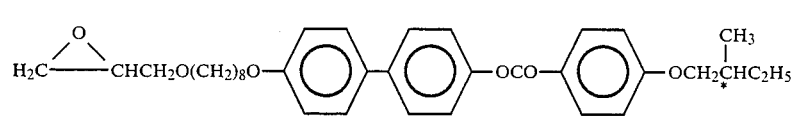 19.
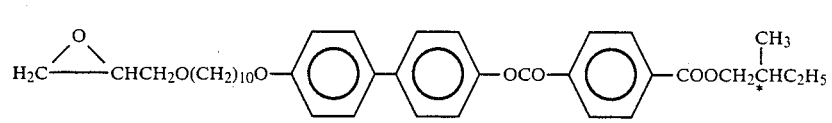 20.
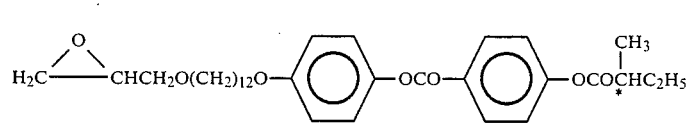 21.
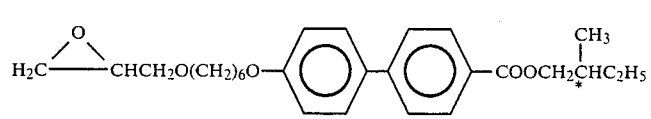 22.
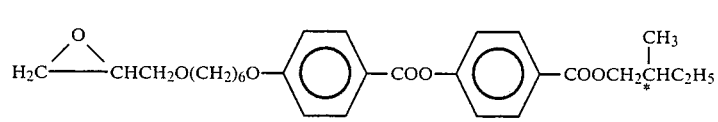 23.
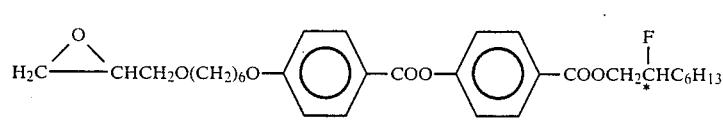 24.
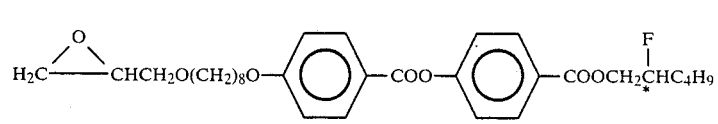 25.
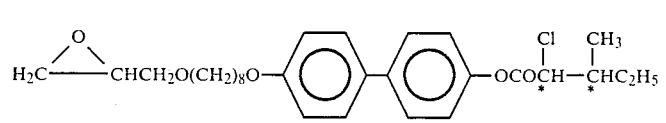 26.
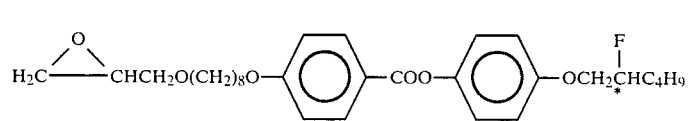 27.
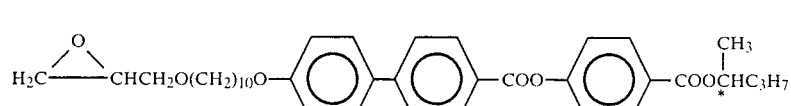 28.

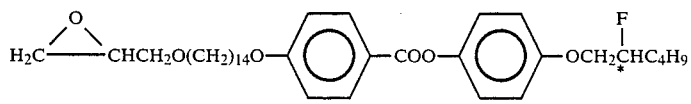

29.

The ferroelectric liquid-crystalline polymers of the present invention are prepared by polymerizing one or more of the monomers thus obtained, and any known method of polymerization such as cationic polymerization may be employed for the preparation.

the catalysts that can be used for the cationic polymerization in the present invention are known ones including protonic acids such as sulfuric acid, phosphoric acid or perchloric acid, lewis acids such as boron trifluoride, aluminum chloride, titanium tetrachloride or stannic chloride, and etherates of boron trifluoride. Among these catalysts, stannic chloride may be suitably used.

It is also possible that the polymers are prepared by coordination polymerization by using organic aluminum complexes, etc. as catalysts. In this case, the polymers having a number average molecular weight of not less than 30,000 can be obtained.

the polymerization techniques that can be employed in the present invention are various known techniques such as bulk polymerization technique, slurry polymerization technique, and solution polymerization technique, and solution polymerization technique may be preferably employed.

The suitable polymerization temperature is not uniformly specified since it varies depending on the kind of the catalyst, but is can be usually from 0° to 30° C.

The suitable polymerization time varies depending on other polymerization conditions including the polymerization temperature, etc., but it can be usually from several hours to six days.

The control of the molecular weight of the polymers can be conducted by addition of a known molecular weight controlling agent and/or by control of the concentration of catalyst to monomers.

When bulk polymerization technique is employed, the polymers may be directly fixed between a couple of substrates in a state of adhering to the substrates by sufficiently mixing one or more monomers with an initiator, sufficiently de-aerating the mixture, introducing the de-aerated mixture between two substrates such as glass substrates, and then heating.

The solvent to be used in slurry polymerization and solution polymerization may be any known inert solvent. The illustrative examples of the solvents to be suitably used include hexane, dichloromethane or aromatic solvents such as benzene, toluene, and xylene.

It is not essential but is preferable to replace the atmosphere of the reaction system with an inert gas such as argon or nitrogen at the time of the polymerization reaction and the above-described conversion reaction to epoxides.

Thus obtained liquid-crystalline polymers may be used in a form of film by forming them by a known film forming technique such as casting technique. T-die technique, inflation technique, calender technique, or stretching technique. Thus obtained films of the polymers of the present invention are applicable in various optoelectronics fields, such as liquid crystal displays, electronic optical shutters, and electronic optical diaphragms, by disposing them between a couple of large glass substrates, curved glass substrates, polyester films, etc., not to mention two usual glass substrates. Further, the polymers may also be directly formed into films adhering to a substrate by dissolving a polymer in a suitable solvent, applying the resulting polymer solution to a surface of a substrate such as glass substrate, and then evaporating the solvent away.

By the measurement of phase transition temperature, it was confirmed that the ferroelectric liquid-crystalline polymers of the present invention exhibit chiral smectic c phase liquid crystal state at a wide temperature range including temperatures around room temperature. It was also confirmed that they have high speeds of response to electric field, for example several milliseconds, at temperatures around room temperature. In addition, the ferroelectric liquid-crystalline polymers of the present invention have another advantage in attaining high contrast ratio when used in optical display devices. These facts indicate that the ferroelectric liquid-crystalline polymers of the present invention are very useful materials which can be used in a wide temperature range including room temperature.

Because the ferroelectric liquid-crystalline polymers of the present invention have both of the properties of liquid crystals having smectic phases and the typical property of polymers, i.e. excellent moldability, they have large possibility of usage in the fields of integrated optics, optoelectronics, and information memory. That is, the polymers of the present invention may be used as various electronic optical devices, for example liquid crystal displays such as digital displays of various forms, electronic optical shutters, optical-path transfer switches in optical communication systems, electronic optical diaphragms, memory devices, optical modulators, liquid crystal optical printer heads, and variable-focal-length.

The ferroelectric liquid-crystalline polymers of the present invention may be further improved, at need, by various treatments well known in this industry, for example mixing two or more polymers of the present invention, mixing with other polymers, addition of additives, such as various inorganic or organic compounds or metals, including stabilizers, plasticizers, etc.

In order to fully and clearly illustrate the present invention, the following examples are presented. It is intended that the examples be considered as illustrative rather than limiting the scope of the invention disclosed and claimed herein.

EXAMPLES 1 TO 12

The structures of the polymers and epoxides obtained in the Examples were identified by NMR, IR, and elementary analysis. The measurement of phase transition temperatures and the identification of phases were each conducted by the use of a DSC and a polarization microscope, respectively. (glass: glass state, Cry: crystal state, S: unidentified smectic phase, SmC*: chiral smectic C phase, SmA: smectic A phase, N: nematic phase, Ch: cholesteric phase, Iso: isotropic phase) The numerals in phase transition behavior schemes represent the phase transition temperatures in °C. unit.

The measurements of the electric field response speed and spontaneous polarization intensity were conducted as follows.

Measurement of Electric Field Response Speed

A polymer was sandwiched between two ITO substrates (20×10 mm) and was adjusted to 25 μm thick with a spacer, and an electric field of $E=2\times10^6$ was then applied, measuring the time of response for the changes of the transmission intensity (0→90%).

Measurement of Spontaneous Polarization Intensity

A polymer was sandwiched between two glass substrates of 0.2 cm² in area each having an ITO circular, transparent electrode and was adjusted to 10 μm thick with a spacer. A triangular voltage having a crest value of 200V was applied thereto, and the spontaneous polarization intensity was calculated from the signal of polarization inversion current that was observed at the time of applying the voltage.

EXAMPLE 1

Synthesis of Monomer nyl chloride, i.e. 20 ml of thionyl chloride, as both a reactant and a solvent, and the mixture was then stirred for 4 hours at 80° C. After the conclusion of the reaction, the residual thionyl chloride was distilled out under reduced pressure to obtain an acid chloride compound.

A toluene solution containing 2.2 g of 2-methylbutyl p-hydroxybenzoate and 1.0 g of pyridine was added dropwise into a toluene solution of the acid chloride compound obtained above. Subsequently, reaction was carried out for one day at room temperature. After the conclusion of the reaction, the reaction mixture was washed with water and dried over magnesium sulfate, and the solvent was then distilled out under reduced pressure. The residue was purified by column chromatography to obtain 2.5 g of the objective phenyl benzoate compound. (Yield: 53%).

The phenyl benzoate compound exhibited liquid crystal state at room temperature.

1.(4) Conversion to epoxide 2.5 g of the phenyl benzoate compound obtained in 1.(3) was dissolved in dichloromethane, and the atmosphere of the system was replaced with argon. To the solution was then added 1.0 g of m-chloroperbenzoic acid, and reaction was carried out for one day at room

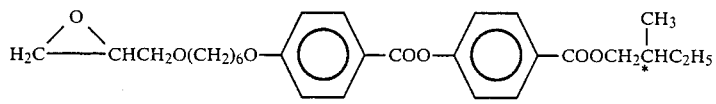

1.(1) Synthesis of 6-bromohexyl allyl ether 5.0 g of allyl alcohol and 65 g of 1,6-dibromohexane were dissolved in 80 ml of hexane. To the obtained solution were added 110 g of 50% aqueous sodium hydroxide solution and 1.5 g of tetrabutylammonium bromide, and the mixture was refluxed for 17 hours. After conclusion of the reaction, hexane phase was corrected, washed with water, and dried over magnesium sulfate. Then, after distilling the solvent out under reduced pressure, the resulting residue was purified by column chromatography to obtain 12.6 g of the objective ω-haloalkyl allyl ether compound. (Yield: 66%).

1.(2) Synthesis of 4-(6-allyloxyhexyloxy)benzoic acid 6.0 g of 6-bromohexyl allyl ether obtained in 1.(1). 4.4 g of methyl p-hydroxybenzoate, and 2.0 g of potassium hydroxide were dissolved in 50 ml of ethanol, and the solution was then refluxed for 12 hours. After addition of 150 ml of an aqueous potassium hydroxide solution (containing 6.0 g of potassium hydroxide), the solution was then further refluxed for 12 hours. After the conclusion of the reaction, hydrochloric acid was added dropwise into the reaction mixture to lower the value of pH to 2, and the generated precipitation was collected. The obtained precipitate was washed sufficiently with water and, then, was dried by heating under reduced pressure, to obtain 6.5 g of the objective carboxylic acid compound. (Yield: 87%).

1.(3) Synthesis of 4'-(2-methylbutyloxycarbonyl)phenyl 4-(6-allyloxyhexyloxy)benzoate Two drops of pyridine were added as a catalyst to 2.8 g of the carboxylic acid compound obtained in 1.(2). To the resulting mixture was added an large excess of thiotemperature. After the conclusion of the reaction, the reaction mixture was washed with an aqueous potassium carbonate solution and was dried over magnesium sulfate, and the solvent was then distilled out under reduced pressure to obtain 2.6 g of a monomer that is the epoxide represented by the above structure. The obtained product was used for the subsequent reaction without conducting any more purification.

The chart of NMR spectrum of the epoxide and each hydrogen being attributed to for each peak in the chart are shown in FIG. 1, and the result of elementary analysis is shown below.

|  | Elementary analysis values | |
| --- | --- | --- |
|  | C (%) | H (%) |
| Calculated values | 69.40 | 7.49 |
| Measured values | 70.9 | 7.6 |

Polymerization 2.6 g of the monomer obtained in 1.(4) was dissolved in dichloromethane, and the atmosphere of the system was replaced with argon. To the solution was then added 20 μl (3 mol % of the monomer) of stannic chloride. Polymerization reaction was carried out for 3 days at room temperature. After the conclusion of the reaction, the reaction solution was concentrated and purified by column chromatography to obtain 1.0 g of the objective polymer having the repeating unit represented by the following formula. (Yield: 38%)

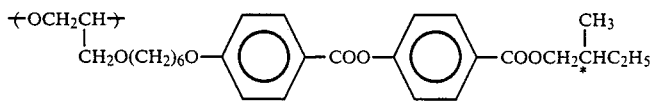

Figure 2:
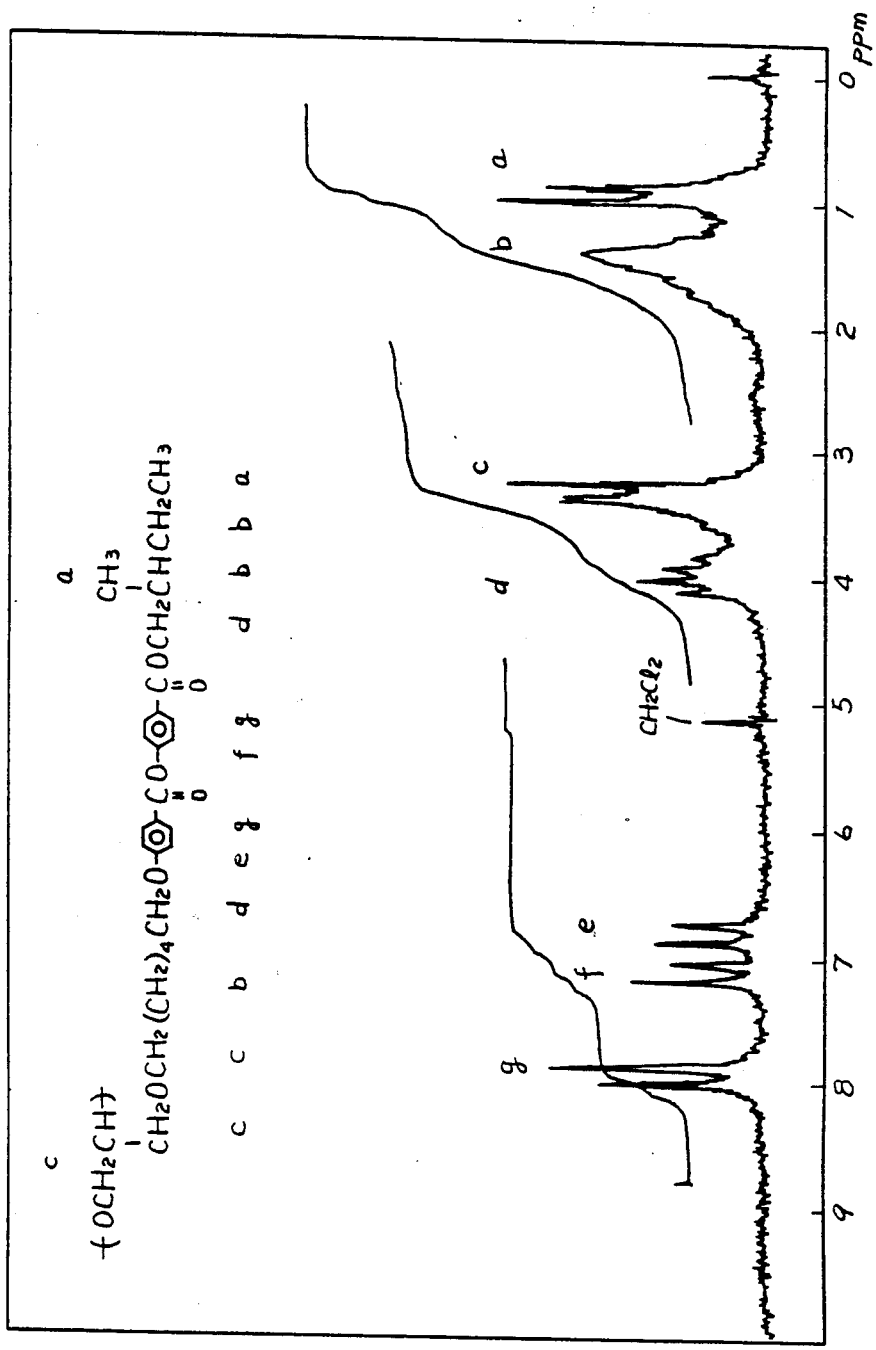
FIG. 2 is a chart of NMR spectrum of the ferroelectric liquid-crystalline polymer obtained in Example 1.

The chart of NMR spectrum of the obtained polymer and each hydrogen being attributed to for each peak in the chart are shown in FIG. 2, and the number average molecular weight, phase transition behavior, spontaneous polarization intensity, and electric field response time of the polymer are shown in Table 1.

EXAMPLE 2

Synthesis of Monomer

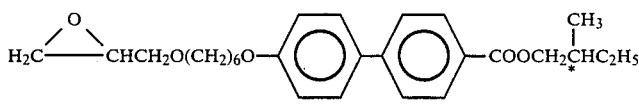

2.(1) Synthesis of 2-methylbutyl 4'-(6-allyloxyhexyloxy)biphenyl-4-carboxylate 6.6 g of 6-bromohexyl allyl ether obtained in 1.(1) in Example 1, 8.5 g of 2-methylbutyl 4-hydroxybiphenyl-4-carboxylate, and 4.2 g of potassium carbonate were heated in 2-butanone at 80° C. for 12 hours with stirring. After the conclusion of the reaction, inorganic matters were removed off by filtration, and the solvent was then distilled out under reduced pressure. The residue was recrystallized from methanol to obtain 4.6 g of the objective biphenyl derivative. (Yield: 36%)

2.(2) Conversion to epoxide 2.5 g of the biphenyl derivative obtained in 2.(1) was dissolved in dichloromethane, and the atmosphere of the system was replaced with argon. After addition of 1.2 g of m-chloroperbenzoic acid, the solution was stirred for 2 days at room temperature. After the conclusion of the reaction, the reaction solution was washed with an aqueous solution containing 2.5 g of potassium carbonate. After drying the reaction solution over magnesium sulfate, the solvent was then distilled out under reduced pressure, to obtain 2.0 g of the objective epoxide represented by the above structural formula. (Yield: 77%)

The obtained monomer was a liquid having a high viscosity at room temperature. The monomer was then used in the subsequent reaction without conducting any more purification.

Figure 3:
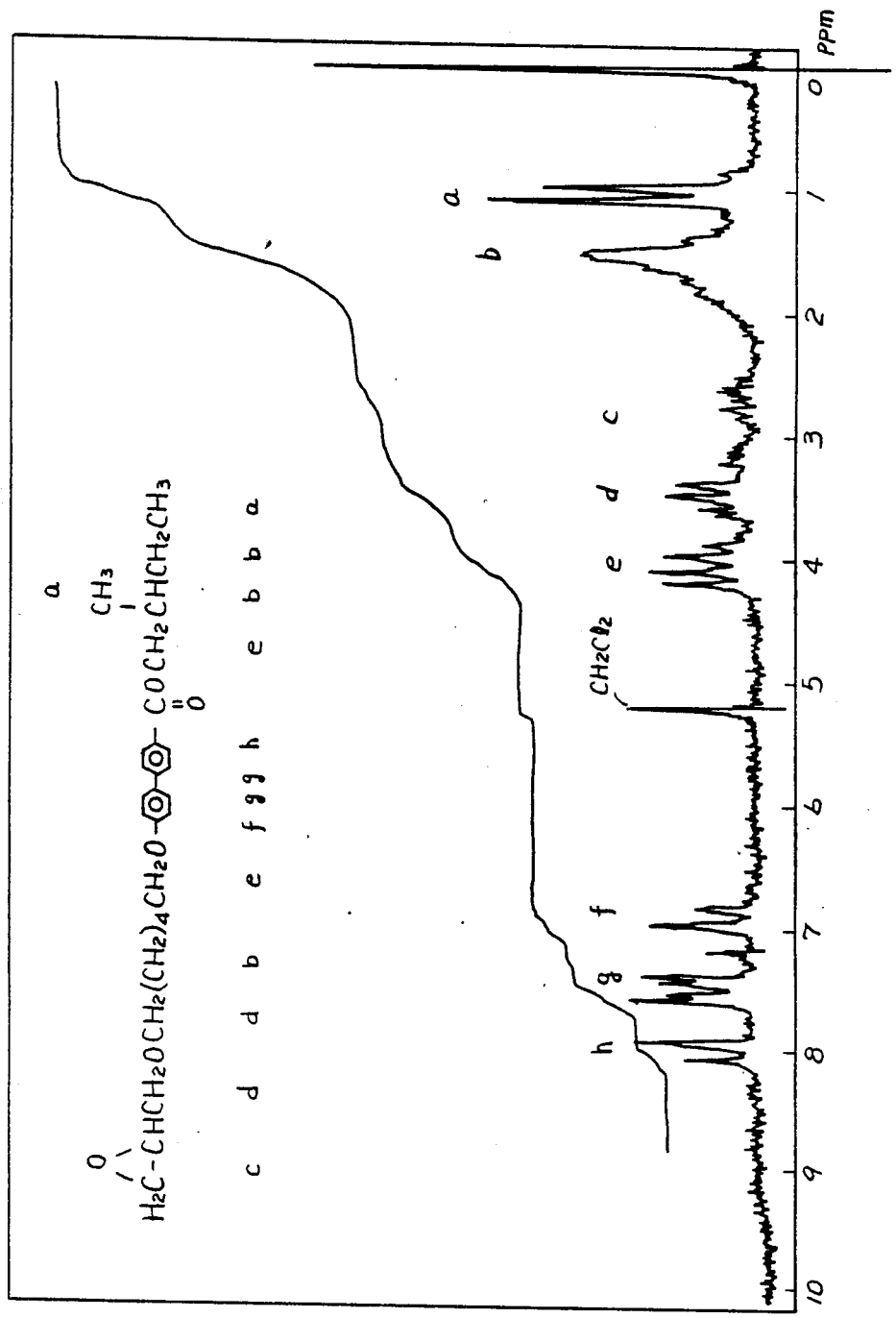
FIG. 3 is a chart of NMR spectrum of the epoxide obtained in Example 2.

The chart of NMR spectrum of the epoxide and each hydrogen being attributed to for each peak in the chart are shown in FIG. 3, and the result of elementary analysis is shown below.

| | Elementary analysis values | |
|---|---|---|
| | C (%) | H (%) |
| Calculated values | 73.61 | 8.24 |
| Measured values | 73.8 | 8.35 |

Polymerization 2.0 g of the monomer obtained in 2.(2) was dissolved in dichloromethane, and the atmosphere of the system was replaced with argon. To the solution was then added 16 μl (3 mol % of the monomer) of stannic chloride. Polymerization reaction was carried out for 4 days at room temperature. After the conclusion of the reaction, the reaction solution was concentrated and was then reprecipitated in methanol. The precipitate was collected and purified by column chromatography, to obtain 0.5 g of the objective polymer having the repeating unit represented by the following formula. (Yield: 25%)

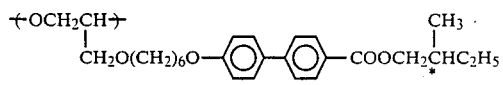

Figure 4:
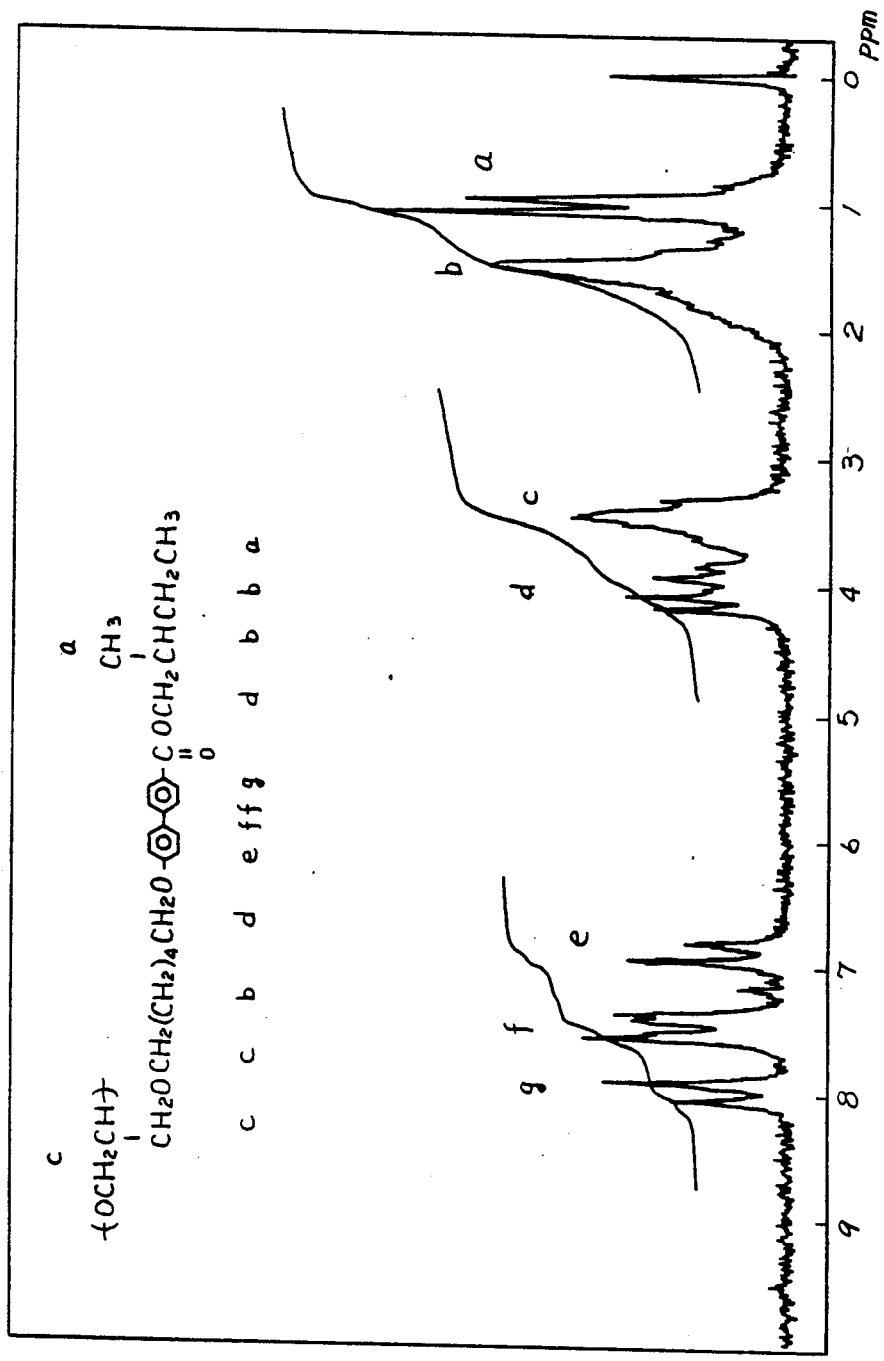
FIG. 4 is a chart of NMR spectrum of the ferroelectric liquid-crystalline polymer obtained in Example 2.

The chart of NMR spectrum of the obtained polymer and each hydrogen being attributed to for each peak in the chart are shown in FIG. 4, and the number average molecular weight, phase transition behavior, spontaneous polarization intensity, and electric field response time of the polymer are shown in Table 1.

EXAMPLE 3

Synthesis of Monomer

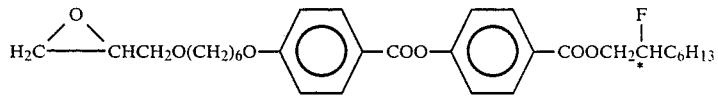

3.(1) Synthesis of 2-fluorooctyl p-hydroxybenzoate

Into an egg-plant flask was placed 7.6 g of p-acetoxybenzoic acid followed by adding 20 ml of thionyl chloride. The mixture was then heated at 80° C. for 4 hours with stirring. After the conclusion of the reaction, the excessive thionyl chloride was distilled out under reduced pressure to obtain an acid chloride compound.

A toluene solution containing 6.4 g of (−)-2-fluoro-1-octanol and 3.5 g of pyridine was added dropwise into a toluene solution of the acid chloride compound obtained above. The obtained mixture was stirred for one day at room temperature. Subsequently, after the reaction solution was washed with water and dried over magnesium sulfate, the solvent was distilled out under reduced pressure. The residue was dissolved in ether, and 15 ml of benzylamine was then added dropwise thereto. The mixture was then stirred at room temperature for 3 hours. The resulting reaction solution was washed with successive, diluted hydrochloric acid and water and was then dried over magnesium sulfate. By distilling the solvent out under reduced pressure and purifying the resulting residue by column chromatography, 8.0 g of the objective ester compound was obtained. (Yield: 71%).

3.(2) Synthesis of 2-fluorooctyl 4-[4'-(6-allyloxyhexyloxy)benzoyloxy]benzoate

Into an egg-plant flask was placed 1.0 g of 4-(6-allyloxyhexyloxy)benzoic acid, and 5 ml of thionyl chloride was added thereto. After the mixture was heated to 80° C., reaction was carried out for 3 hours. After the conclusion of the reaction, the excessive thionyl chloride was distilled out under reduced pressure to obtain an acid chloride compound.

A toluene solution containing 1.0 g of 2-fluorooctyl p-hydroxybenzoate and 0.4 g of pyridine was added dropwise into a toluene solution of the acid chloride compound obtained above. The resulting mixture was stirred for one day at room temperature. After conclusion of the reaction, the reaction solution was washed with water and dried over magnesium sulfate and, then, the solvent was distilled out under reduced pressure. The residue was purified by column chromatography to obtain 0.8 g of the objective phenyl benzoate compound. (Yield: 42%).

3.(3) Conversion to epoxide 0.8 of the phenyl benzoate compound obtained in 3.(2) was dissolved in dichloromethane, and the atmosphere of the system was replaced with argon. After addition of 0.3 g of m-chloroperbenzoic acid, the mixture was stirred for one day at room temperature. After the conclusion of the reaction, the reaction solution was washed with an aqueous potassium carbonate solution. After drying the reaction solution over magnesium sulfate, the solvent was distilled out under reduced pressure to obtain 0.6 g of a monomer that is the epoxide represented by the above structural formula. (Yield: 75%).

Figure 5:
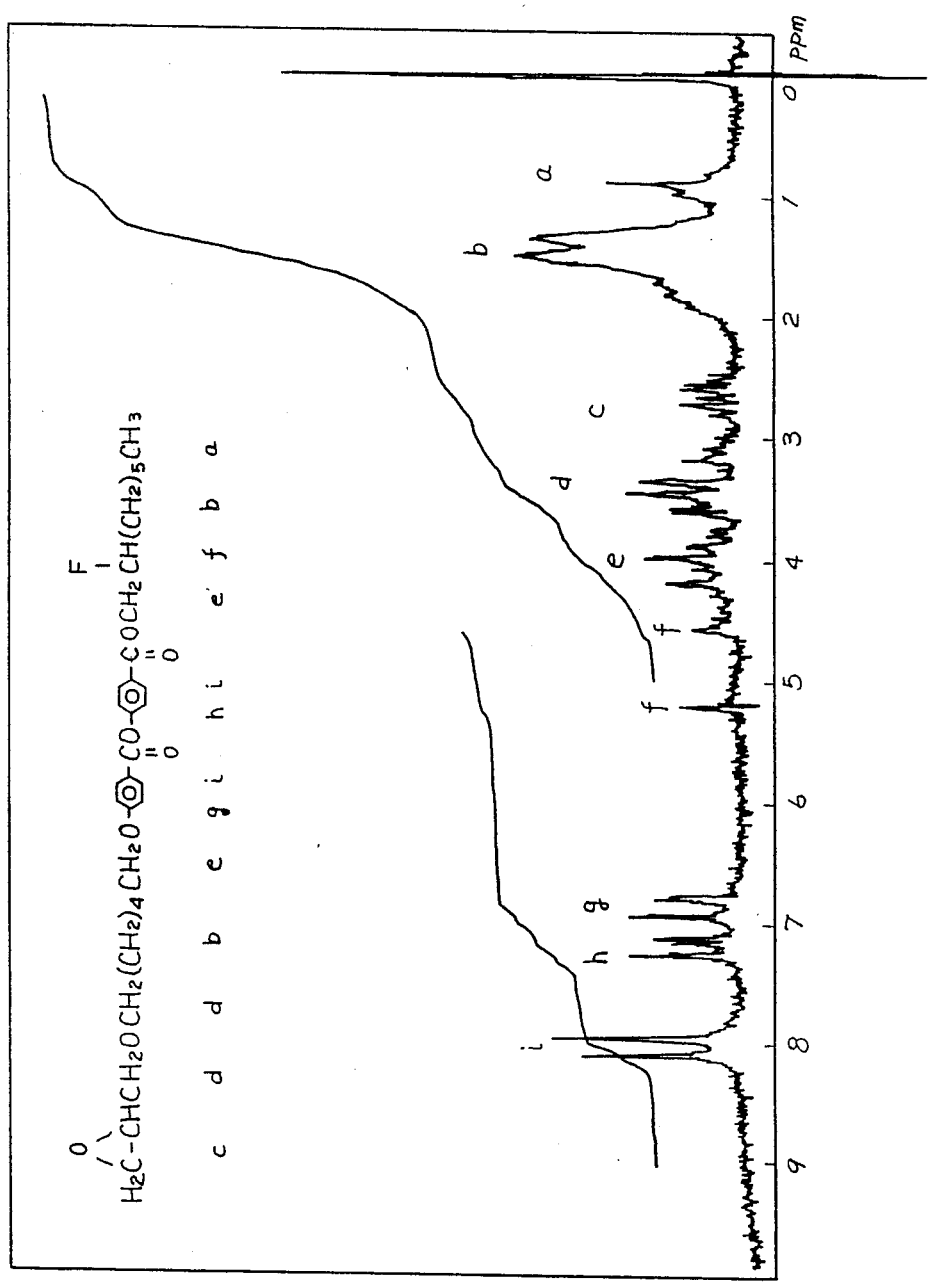
FIG. 5 is a chart of NMR spectrum of the epoxide obtained in Example 3.

The chart of NMR spectrum of the epoxide and each hydrogen being attributed to for each peak in the chart are shown in FIG. 5, and the result of elementary analysis is shown below.

|  | Elementary analysis values | | |
| --- | --- | --- | --- |
|  | C (%) | H (%) | F (%) |
| Calculated values | 68.36 | 7.59 | 3.49 |
| Measured values | 69.1 | 7.7 | 3.5 |

Polymerization 0.6 g of the monomer obtained in 3.(3) was dissolved in dichloromethane, and the atmosphere of the system was replaced with argon. To the solution was then added 4 μl of stannic chloride. Polymerization reaction was carried out for 2 days at room temperature. After the conclusion of the reaction, the reaction solution was concentrated and purified by column chromatography to obtain 0.4 g of the objective polymer having the repeating unit represented by the following formula. (Yield: 67%).

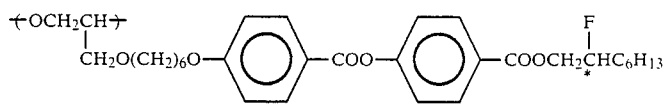

Figure 6:
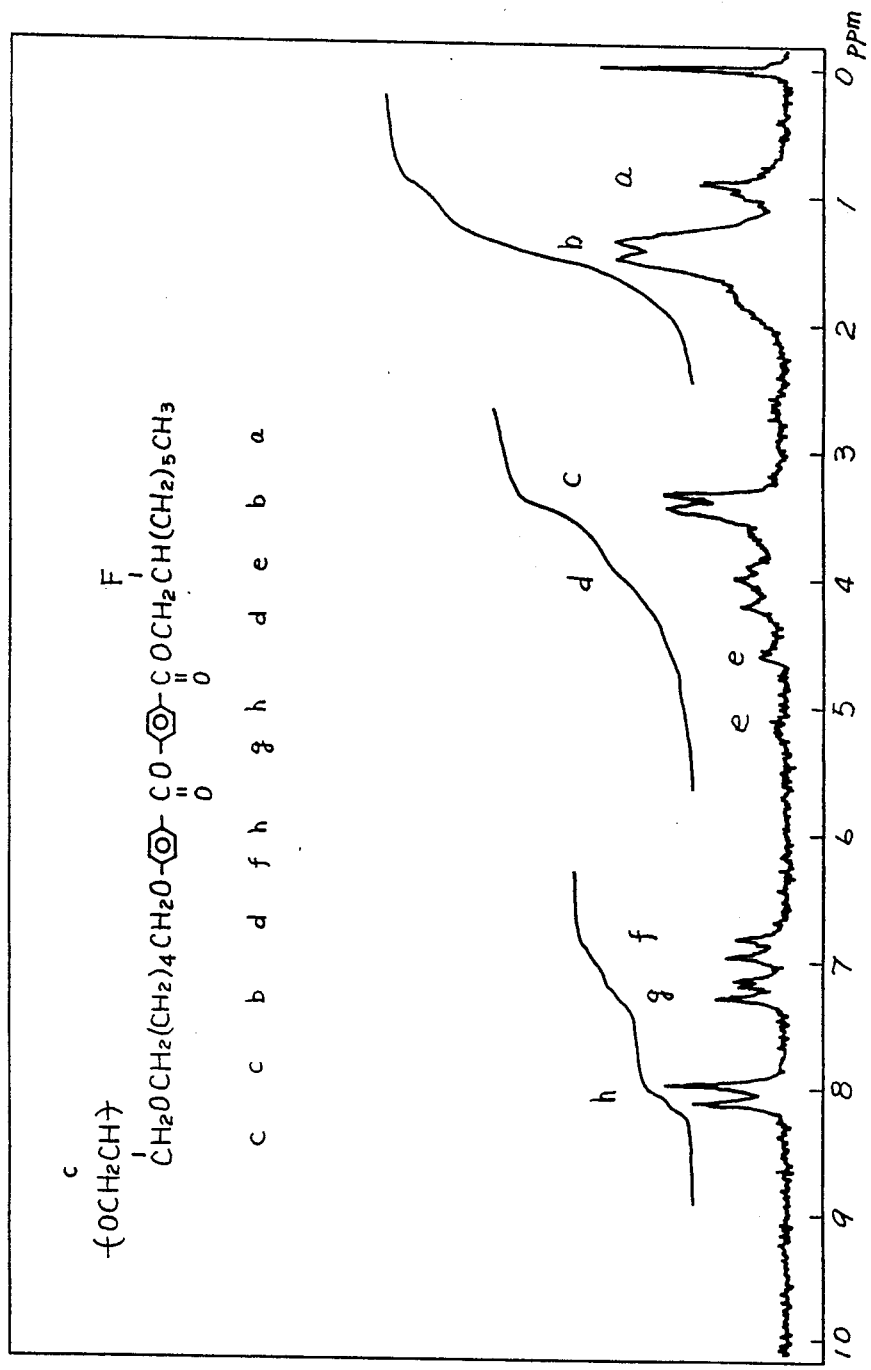
FIG. 6 is a chart of NMR spectrum of the ferroelectric liquid-crystalline polymer obtained in Example 3.

The chart of NMR spectrum of the obtained polymer and each hydrogen being attributed to for each peak in the chart shown in FIG. 6, and the number average molecular weight, phase transition behavior, spontaneous polarization intensity, and electric field response time of the polymer are shown in Table 1.

EXAMPLE 4

Synthesis of Monomer

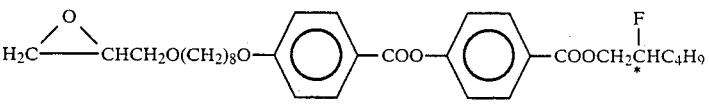

4.(1) Synthesis of 8-bromooctyl allyl ether 3.5 g of allyl alcohol was dissolved in 50 ml of THF. To the solution was added 2.5 g of 60% sodium hydride (a mixture of sodium hydride and a mineral oil having a sodium hydride content of 60% weight) little by little. After stirring the mixture for 30 minutes at room temperature, a solution consisting of 33 g of 1.8-dibromooctane and 10 ml of THF was added dropwise to the mixture. After the conclusion of the dropping, the temperature was raised to reflux the mixture for 12 hours. After the conclusion of the reaction, the remaining sodium hydride was decomposed by adding a small amount of water. After distilling THF out under reduced pressure, dichloromethane and water were then added to the remaining reaction mixture, and the resulting mixture was shaken. The dichloromethane layer was collected and was dried over magnesium sulfate. After concentrating the dried dichloromethane layer under reduced pressure, the residue was purified by column chromatography to obtain 8.6 g of the objective ω-haloalkyl allyl ether. (Yield: 57%).

4.(2) Synthesis of 4-(8-allyloxyoctyloxy)benzoic acid

The procedure in 1.(2) in Example 1 was repeated with the exception that 7.7 g of 8-bromooctyl allyl ether obtained in 4.(1) was used in place of 6-bromohexyl allyl ether used in 1.(2) in Example 1, to obtain 7.3 g of the objective carboxylic acid compound. (Yield: 80%).

4.(3) Synthesis of 2-fluorohexyl p-hydroxybenzoate

The procedure of 3.(1) in Example 3 was repeated with the exception that 4.0 g of (−)-2-fluro-1-hexanol was used in place of (−)2-fluro-1-octanol used in 3.(1) in Example 3, to obtain 5.4 g of the objective product. (Yield: 74%).

4.(4) Synthesis of 2-fluorohexyl 4-[4'-(8-allyloxyoctyloxy)benzoyloxy]benzoate

The procedure in 3.(2) in Example 3 was repeated with the exception the 4.4 g of the carboxylic acid compound obtained in 4.(2) and 3.6 g of the compound obtained in 4.(3) were used, to obtain 4.2 g of the objective phenyl benzoate compound. (Yield: 58%).

4.(5) Conversion to epoxide 4.1 g of the phenyl benzoate compound obtained in 4.(4) was dissolved in dichloromethane, and the atmosphere of the system was then replaced with argon. After addition of 2.0 g of m-chloroperbenzoic acid, the mixture was stirred for one day at room temperature. After the conclusion of the reaction, the reaction solution was washed with an aqueous potassium carbonate solution. After drying the reaction solution over magnesium sulfate, the solvent was then distilled out under reduced pressure to obtain 4.1 of the objective monomer that is the epoxide represented by the above structural formula. (Yield: 97%).

Figure 7:
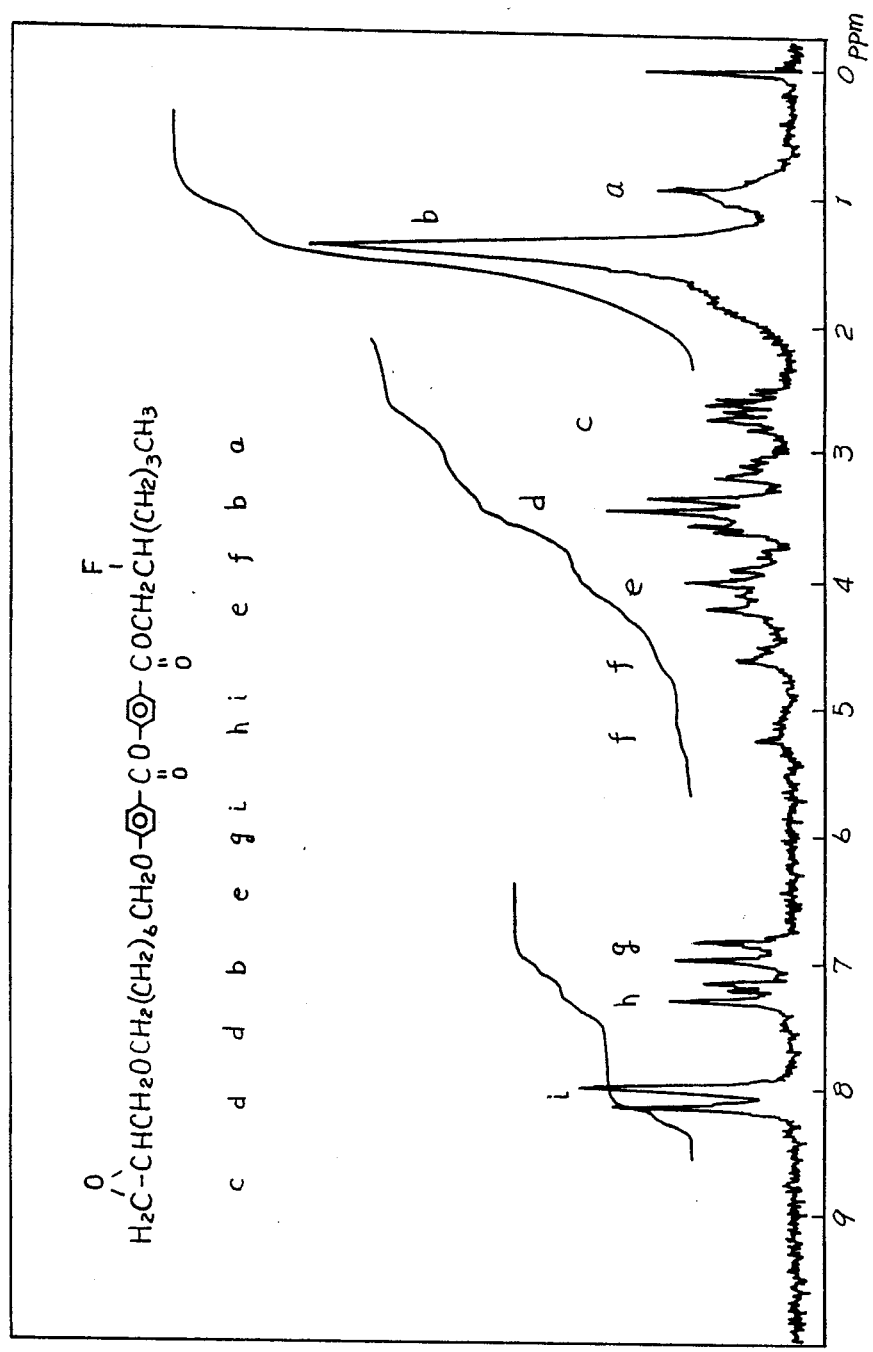
FIG. 7 is a chart of NMR spectrum of the epoxide obtained in Example 4.

The chart of NMR spectrum of the epoxide and each hydrogen being attributed to for each peak in the chart are shown in FIG. 7, and the result of elementary analysis and phase transition behavior are shown below.

|  | Elementary analysis values | | |
| --- | --- | --- | --- |
|  | C (%) | H (%) | F (%) |
| Calculated values | 68.36 | 7.59 | 3.49 |
| Measured values | 68.2 | 7.6 | 3.45 |

Phase Transition Behavior

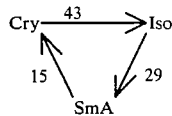

Polymerization 2.0 g of the monomer obtained in 4.(5) was dissolved in dichloromethane, and the atmosphere of the system was replaced with argon. To the solution was then added 13 μl of stannic chloride. Polymerization reaction was carried out for 3 days at room temperature. After the conclusion of the reaction, the reaction solution was concentrated and purified by column chromatography to obtain 1.5 of the objective polymer having the repeating unit represented by the following formula, (Yield: 75%).

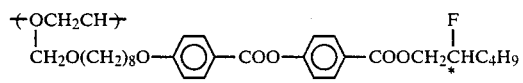

Figure 8:
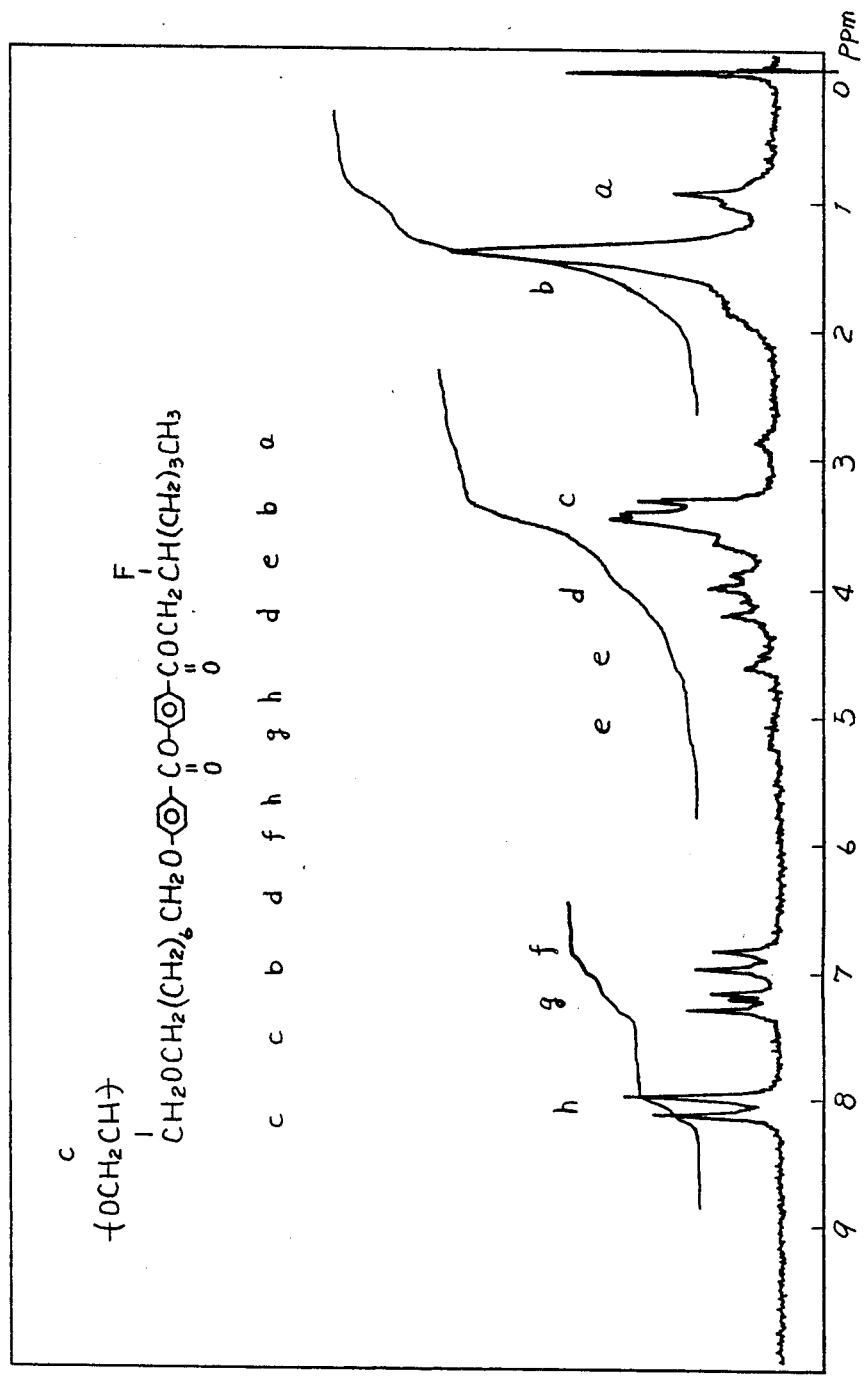
FIG. 8 is a chart of NMR spectrum of the ferroelectric liquid-crystalline polymer obtained in Example 4.

The chart of NMR spectrum of the obtained polymer and each hydrogen being attributed to for each peak in the chart are shown in FIG. 8, and the number average molecular weight, phase transition behavior, spontaneous polarization intensity, and electric field response time of the polymer are shown in Table 1.

EXAMPLE 5

Synthesis on Monomer

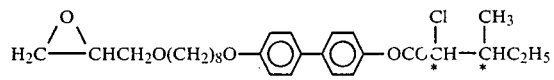

5.(1) Synthesis of 4-(8-allyloxyoctyloxy)-4'-hydroxybiphenyl

A mixture of 5.0 g of 8-bromooctyl allyl ether obtained by the same procedure in 4.(1) in Example 4, 12 g of biphenyl-4,4'-diol, and 9.0 g of potassium hydroxide was refluxed in ethanol for 20 hours. After the conclusion of the reaction, the inorganic matters were removed away by heat filtration. After distilling ethanol out under reduced pressure, the residue was dissolved in a solvent mixture of water and acetone. Diluted hydrochloric acid was added to the obtained solution to lower the value of pH to 2. Subsequently, the solution was heated to evaporate acetone and was then filtered during heating to collect the insoluble matters. The collected insoluble matters were recrystallized from ethanol to obtain 3.5 g of the objective biphenyl derivative. (Yield: 49%).

5.(2) Synthesis of 4-(8-allyloxyoctyloxy)-4'-(2-chloro-3-methylpentanoyloxy)biphenyl 1.5 g of the biphenyl derivative obtained in 5.(1) and 1.0 g of 2-chloro-3-methylpentanoic acid were dissolved in dichloromethane. To the resulting solution were added 1.3 g of dicyclohexylcarbodimide and 0.1 g of 4-pyrrolidinopyridine, and the mixture was stirred for one day at room temprature. After the conclusion of the reaction, the insoluble matters were removed away by filtration, and the resulting solution was washed with water. After drying the solution over magnesium sulfate, the solvent was distilled out under reduced pressure. The residue was purified by column chromatography to obtain 1.0 g of the objective biphenyl derivative. (Yield: 48%).

5.(3) Conversion to epoxide 1.0 g of the biphenyl derivative obtained in 5.(2) was dissolved in dichloromethane, and the atmosphere of the system was replaced with argon. After addition of 0.5 g of m-chloroperbenzoic acid, the mixture was stirred for one day at room temperature. After the conclusion of the reaction, the reaction solution was washed with an aqueous potassium carbonate solution and was further washed with water. After drying the reaction solution over magnesium sulfate, the solvent was distilled out under reduced pressure, to obtain 0.8 g of the objective monomer that is the epoxide represented by the above structural formula. (Yield: 77%).

Figure 9:
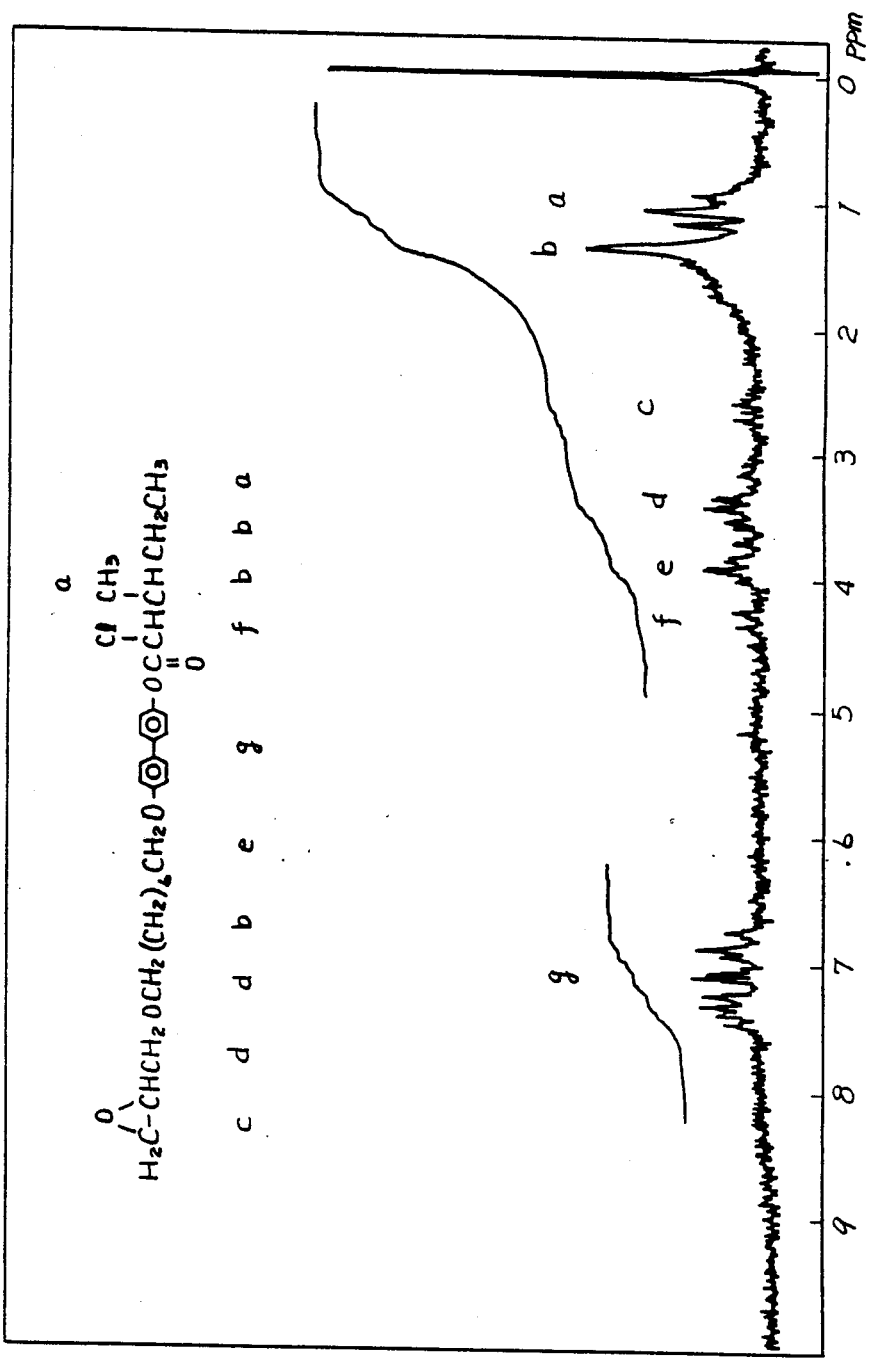
FIG. 9 is a chart of NMR spectrum of the epoxide obtained in Example 5.

The chart of NMR spectrum of the epoxide and each hydrogen being attributed to for each peak in the chart are shown in FIG. 9, ad the result of elementary analysis is shown below.

|  | Elementary analysis values | | |
| --- | --- | --- | --- |
|  | C (%) | H (%) | Cl (%) |
| Calculated values | 69.24 | 7.81 | 7.05 |
| Measured values | 70.2 | 7.7 | 6.6 |

Polymerization 0.8 g of the monomer obtained in 5.(3) was dissolved in dichloromethane, and the atmosphere of the system was replaced with argon. To the solution was then added 5 82 l of stannic chloride. Polymerization reaction was carried out for 2 days at room temperature. After the conclusion of the reaction, the reaction solution was concentrated and purified by column chromatography to obtain 0.5 g of the objective polymer having the repeating unit represented by the following formula. (Yield: 63%).

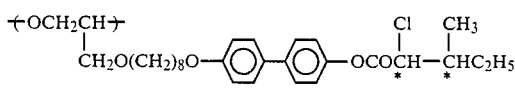

Figure 10:
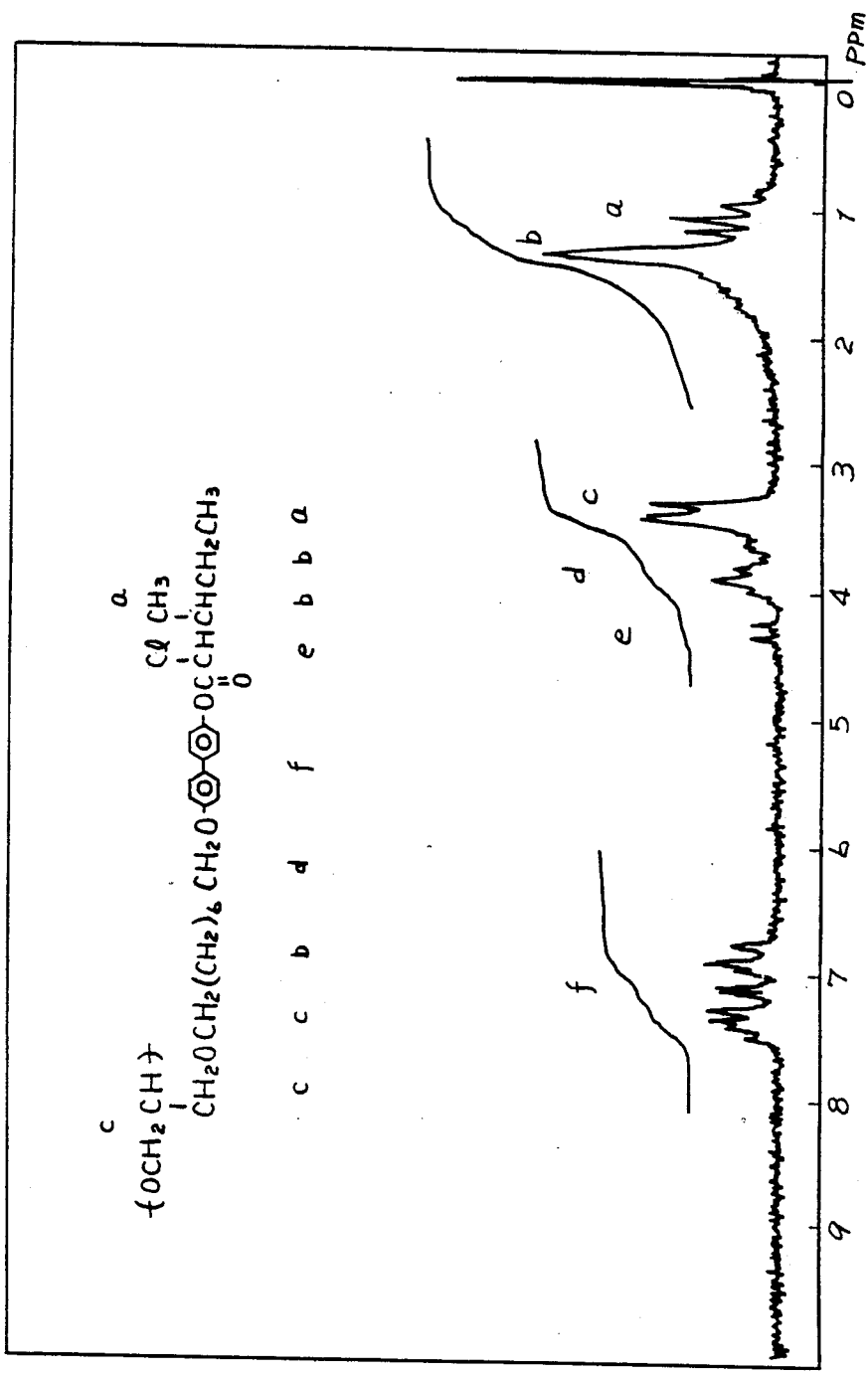
FIG. 10 is a chart of NMR spectrum of the ferroelectric liquid-crystalline polymer obtained in Example 5.

The chart of NMR spectrum of the obtained polymer and each hydrogen being attributed to for each peak in the chart are shown in FIG. 10, and the number average molecular weight, phase transition behavior, spontaneous polarization intensity, and electric field response time of the polymer are shown in Table 1.

EXAMPLE 6

Synthesis of Monomer

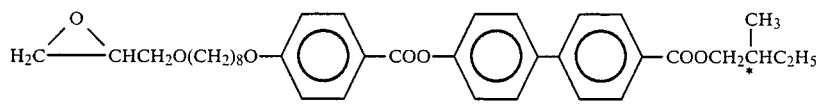

6.(1) Synthesis of 2-methylbutyl 4′-[4′-(8-allyloxyocyloxy)benzoyloxy]biphenyl-4-carboxylate The procedure in 3.(2) in Example 3 was repeated with the exception that 2.8 g of the carboxylic acid compound obtained in 4.(2) in Example 4 and 2.6 g of 2-methylbutyl 4′-hidroxybiphenyl-4-carboxylate were used, to obtain 3.0 g of the objective biphenyl benzoate compound. (Yield: 58%).

6.(2) Conversion to epoxide 1.5 g of the biphenyl benzoate compound obtained in 6.(1) was dissolved in dichloromethane, and the atmosphere of the system was replaced with argon. After addition of 0.6 g of m-chloroperbenzoic acid, the mixture was stirred for 7 hours at room temperature. After the conclusion of the reaction, the reaction solution was washed with an aqueous potassium carbonate solution. After drying the reaction solution over magnesium sulfate, the solvent was distilled out under reduced pressure to obtain 1.5 g of the objective monomer that is the epoxide represented by the above structural formula. (Yield: 97%).

Figure 11:
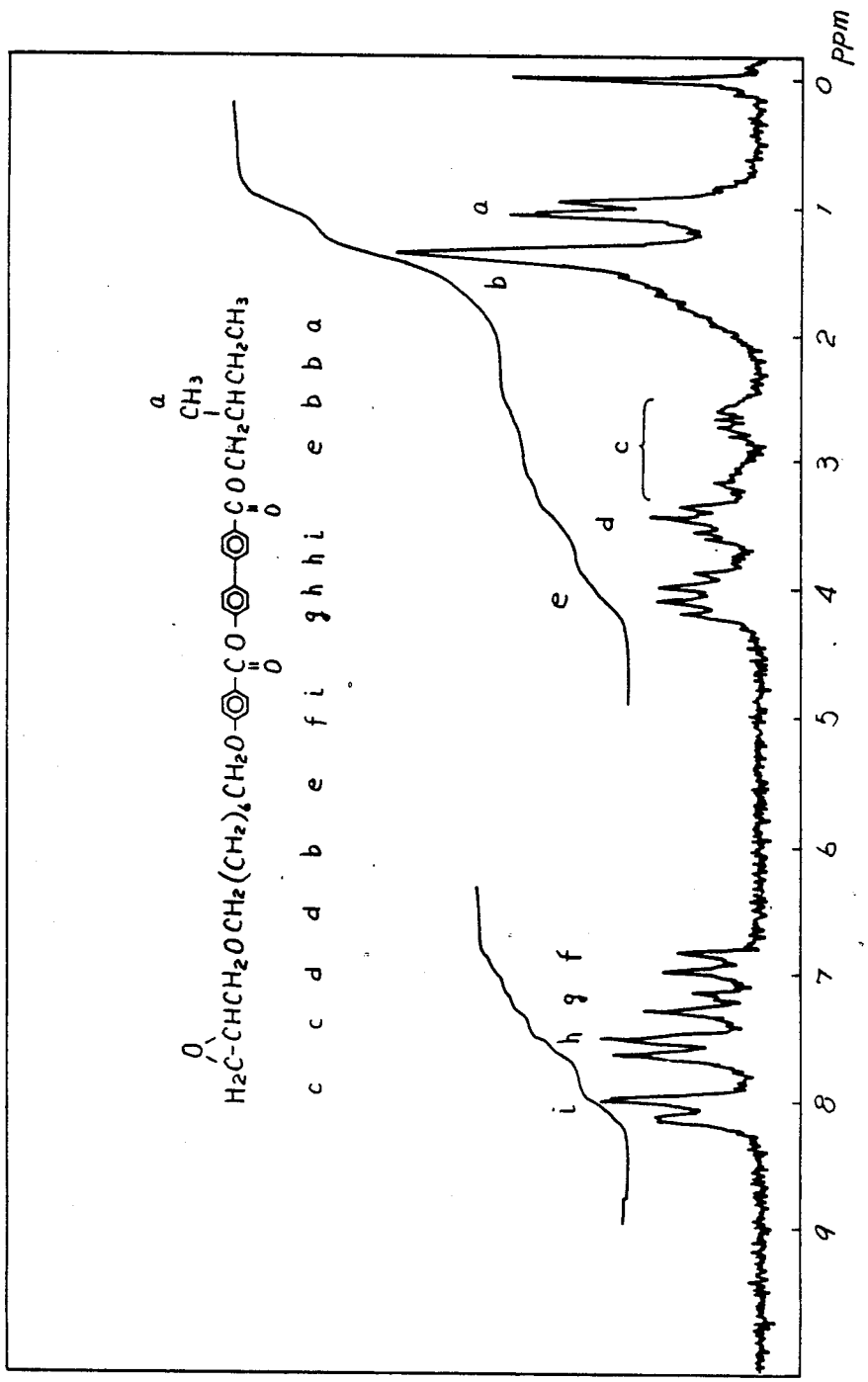
FIG. 11 is a chart of NMR spectrum of the epoxide obtained in Example 6.

The chart of NMR spectrum of the epoxide and each hydrogen being attributed to for each peak in the chart are shown in FIG. 11, and the result of elementary analysis is shown below.

|  | Elementary analysis values | |
| --- | --- | --- |
|  | C (%) | H (%) |
| Calculated values | 73.44 | 7.53 |
| Measured values | 73.6 | 7.5 |

Polymerization 1.5 g of the monomer obtained in 6.(2) was dissolved in dichloromethane, and the atmosphere of the system was replaced with argon. To the solution was then added 15 μl of stannic chloride. Polymerization reaction was carried out for 30 hours at room temperature. After the conclusion of the reaction, the reaction solution was concentrated and purified by column chromatography to obtain 0.9 g of the objective polymer having the repeating unit represented by the following formula. (Yield: 60%).

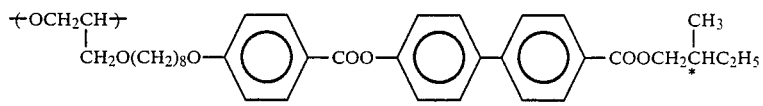

Figure 12:
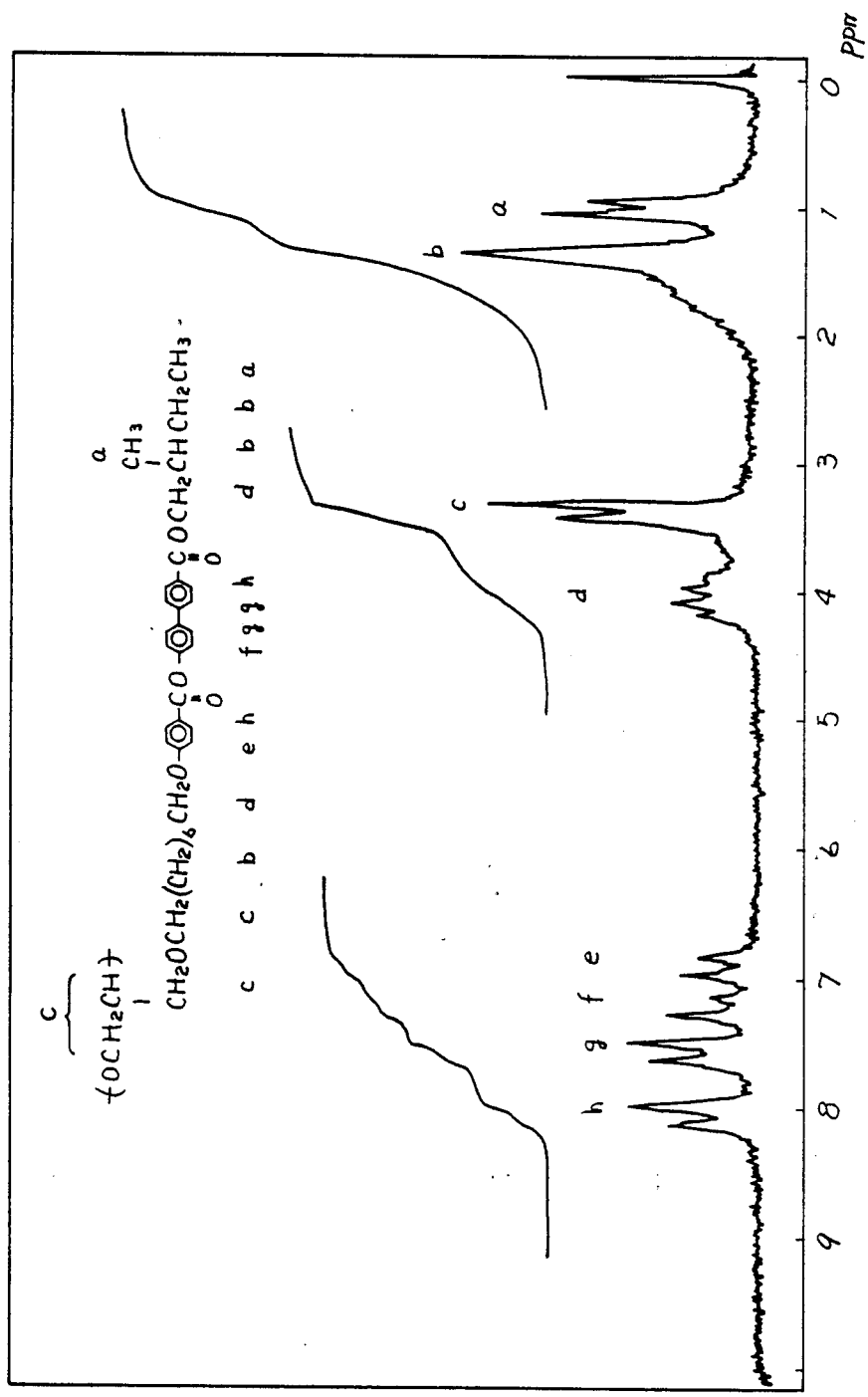
FIG. 12 is a chart of NMR spectrum of the ferroelectric liquid-crystalline polymer obtained in Example 6.

The chart of NMR spectrum of the obtained polymer and each hydrogen being attributed to for each peak in the chart are shown in FIG. 12, and the number average molecular weight, phase transition behavior, spontaneous polarization intensity, and electric field response time of the polymer are shown in Table 2.

EXAMPLE 7

Synthesis of monomer

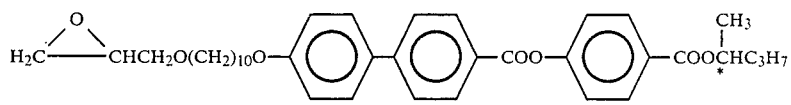

7.(1) Snythesis of 10-iododecyl allyl ether

The reaction and procedure in 4.(1) in Example 4 were repeated with the exception that 2.0 g of allyl alcohol, 1.5 g of 60% sodium hydride, and 33.0 g of 1,10-diiododecane were used, to obtain 8.2 g of the objective ω-haloalkyl allyl ether. (Yield: 53%).

7.(2) Synthesis of 4′-(10-allyloxydecyloxy)biphenyl-4-carboxylic acid

A mixture of 8.2 g of 10-iododecyl allyl ether, 4.8 g of 4′-hydroxybiphenyl-b-carboxylic acid, 3,3 g of potassium hydroxide, and 5.0 g of water was reacted by refluxing the mixture in 50 ml of methanol for 24 hours. After adding 500 ml of water to the resulting reaction mixture, hydrochloric acid was added dropwise to the reaction mixture to lower the value of pH to 2. The resulting precipitate was collected and dried under reduced pressure. The crude product was recrystallized from acetic acid to obtain 4.3 g of the objective carboxylic acid compound. (Yield: 53%).

7.(3) Synthesis of 1-methylbutyl 4-hydroxybenzoate

Three drops of pyridine were added as a catalyst to 5.7 g of 4-acetoxybenzoic acid. To the mixture was added a solution consisting of 50 ml of toluene and 10 ml of thionyl chloride, and the resulting mixture was stirred for 3 hours at 80° C. After the conclusion of the reaction, toluene and the excessive thionyl chloride were distilled out under reduced pressure, to obtain an acid chloride compound.

a toluene solution of the acid chloride compound obtained above was added dropwise to a toluene solution containing 2.5 g of (R)-(—)-2-pentanol and 3.4 g of triethylamine, and the mixture was stirred at room temperature for 5 hours. After the conclusion of the reaction, the reaction mixture was washed with water and dried over magnesium sulfate, and then the solvent was distilled out under reduced pressure to obtain an ester compound.

The above ester compound was dissolved in ether, and 4.0 g of benzylamine was added to the solution. After reaction was carried out for 3 hours at room temperature with stirring, the resulting reaction mixture was washed with the successive, diluted hydrochloric acid and water, and was then dried over magnesium sulfate. The solvent was then distilled out under reduced pressure. The residue was purified by column chromatography to obtain 4.8 g of the objective ester compound. (Yield: 73%).

7.(4) Synthesis of 4″-(1-methylbutyloxycarbonyl)phenyl 4′-(10-allyloxydecyloxy)biphenyl-4-carboxylate Three drops of pyridine and 5.0 g of thionyl chloride were added to 4.3 g of the carboxylic acid obtained in 7.(2), and the mixture was then stirred at 90° C. for 4 hours. After the conclusion of the reaction, the excessive thionyl chloride was distilled out under reduced pressure, to obtain an acid chloride compound. A toluene solution of the acid chloride compound obtained above was added dropwise to a toluene solution containing 2.2 g of the ester compound obtained in 7.(3) and 0.9 g of pyridine, and the mixture was then stirred for one day at room temperature. After the conclusion of the reaction, the reaction solution was washed with water and dried over magnesium sulfate, and the solvent was then distilled out under reduced pressure. The residue was recrystallized from methanol to obtain 5.4 g of the objective phenyl biphenylcarboxylate compound. (Yield: 86%).

7.(5) Conversion to epoxide 2.7 g of the phenyl biphenylcarboxylate compound obtained in 7.(4) was dissolved in dichloromethane, and the atmosphere of the system was replaced with argon. After addition of 1.0 g of m-chloroperbenzoic acid, the mixture was stirred for 7 hours at room temperature. After the conclusion of the reaction, the reaction solution was washed with an aqueous potassium carbonate solution. After drying the reaction solution over magnesium sulfate, the solvent was distilled out under reduced pressure, to obtain 2.5 g of the objective monomer that is the epoxide represented by the above structural formula. (Yield: 90%).

Figure 13:
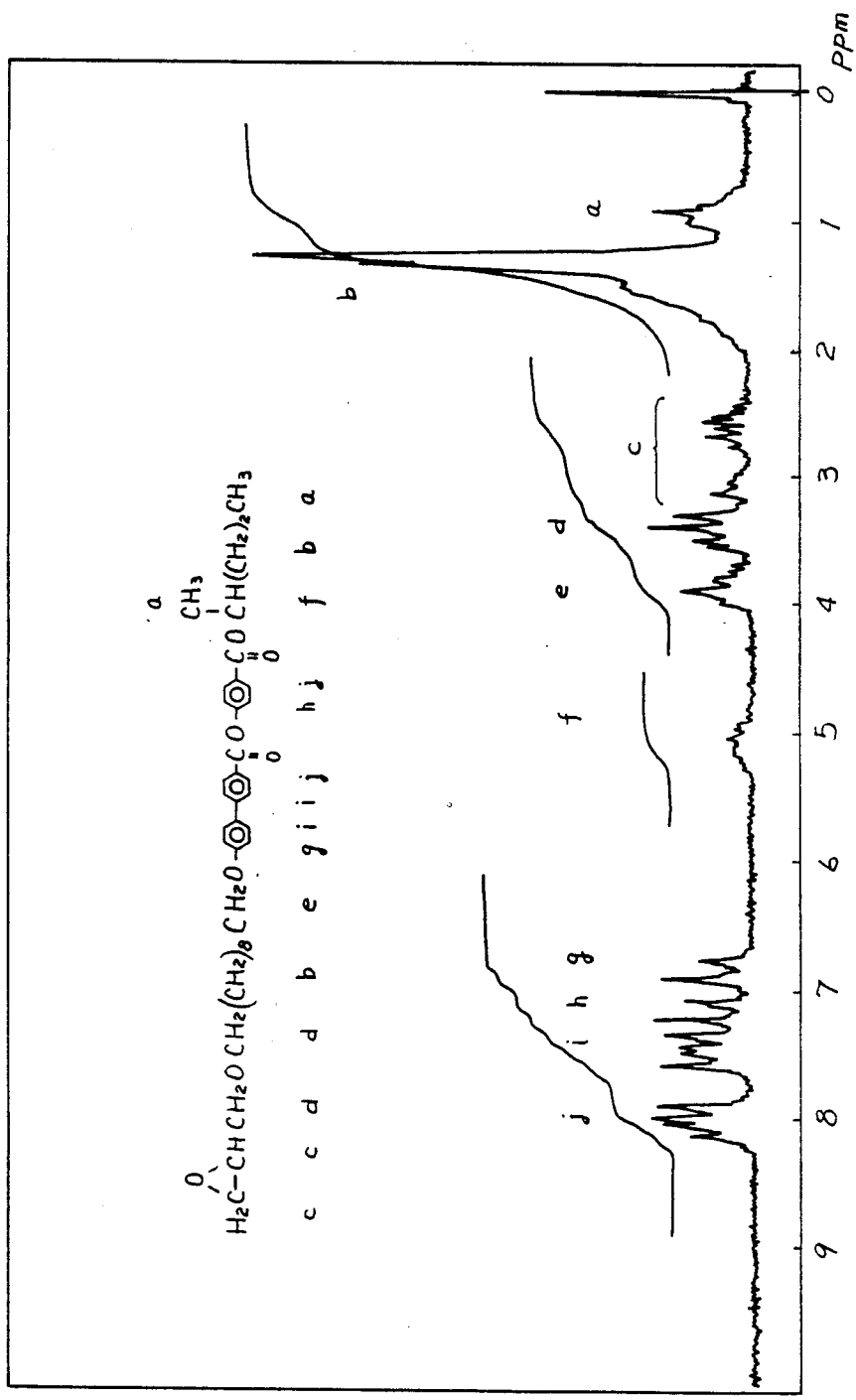
FIG. 13 is a chart of NMR spectrum of the epoxide obtained in Example 7.

The chart of NMR spectrum of the epoxide and each hydrogen being attributed to for each peak in the chart are shown in FIG. 13, and the result of elementary analysis is shown below.

|  | Elementary analysis values | |
|---|---|---|
|  | C (%) | H (%) |
| Calculated values | 74.00 | 7.84 |
| Measured values | 74.2 | 7.8 |

Polymerization 2.5 g of the monomer obtained in 7.(5) was dissolved in dichloromethane, and the atmosphere of the system was replaced with argon. To the solution was then added 24 μl of stannic chloride. Polymerization reaction was carried out for 30 hours at room temperature. After the conclusion of the reaction, the reaction solution was concentrated and purified by column chromatography to obtain 2.1 g of the objective polymer having the repeating unit represented by the following formula. (Yield: 84%).

Figure 14:
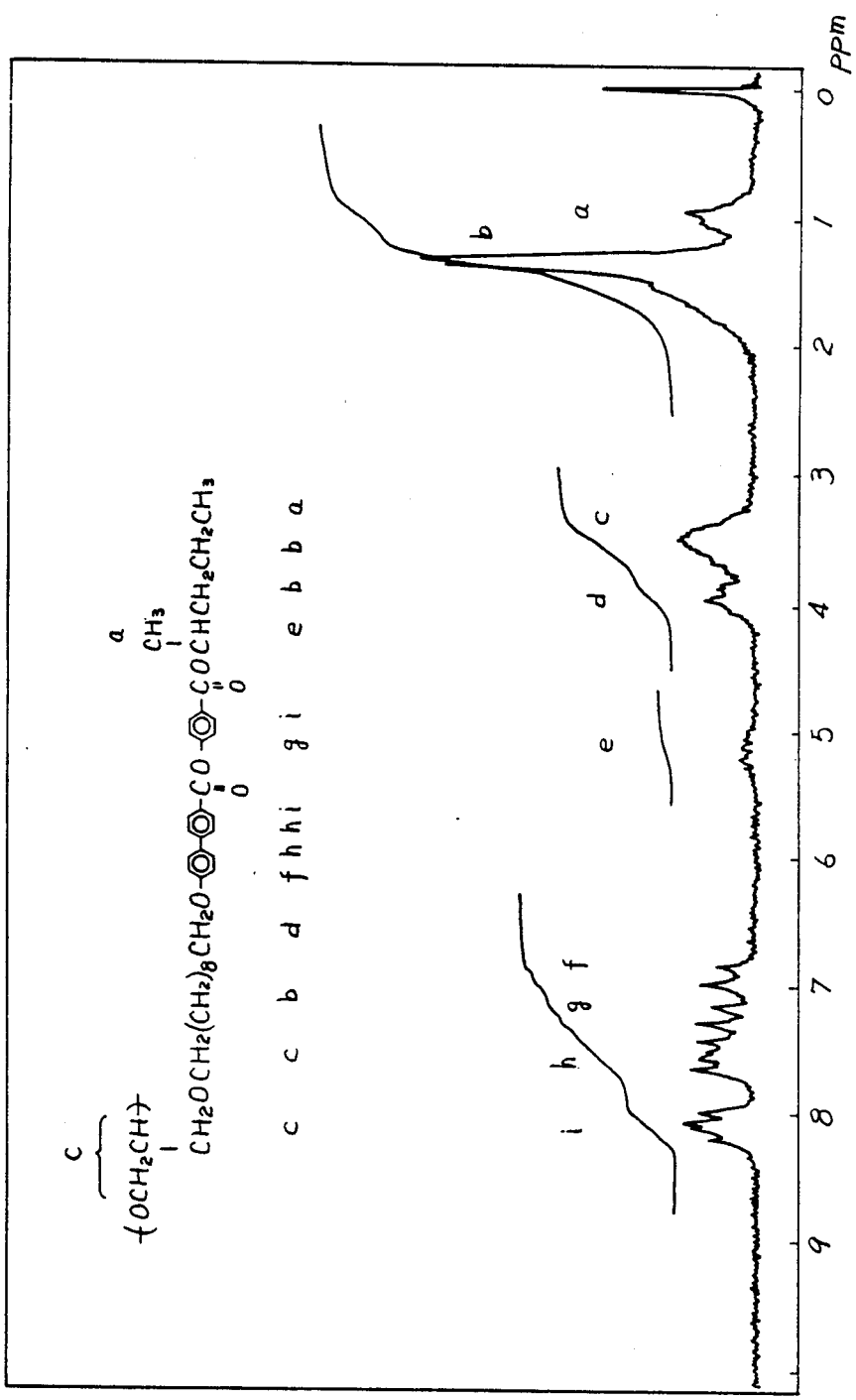
FIG. 14 is a chart of NMR spectrum of the ferroelectric liquid-crystalline polymer obtained in Example 7.

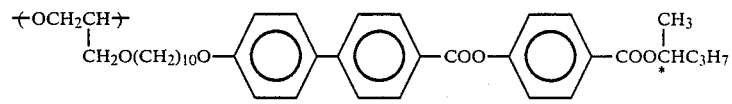

the chart of NMR spectrum of the obtained polymer and each hydrogen being attributed to for each peak in the chart are shown in FIG. 14, and the number average molecular weight, phase transition behavior, spontaneous polarization intensity, and electric field response time of the polymer are shown in Table 2.

EXAMPLE 8

Synthesis of Monomer

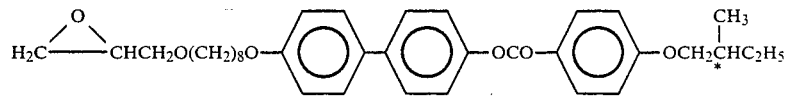

8.(1) Synthesis of 4-[4′-(8-allyloxyoctyloxy)phenyl]-phenol

A mixture of 7.0 g of 8-bromooctyl allyl ether, 11.0 g of biphenyl-4,4′-diol, and 8.0 g of potassium hydroxide was refluxed in methanol for 20 hours. After distilling methanol out under reduced pressure, acetone was added to the resulting solution, and hydrochloric acid was then added dropwise to the solution. After removing the insoluble matters away by filtration, the solvent was distilled out under reduced pressure. The residue was recrystallized from ethanol to obtain 7.2 g of the objective phenol compound. (Yield: 72%).

8.(2) Synthesis of 4-(2-methylbutyloxy)benzoic acid 10.0 g of S-(—)-2-methylbutanol was dissolved in 100 ml of pyridine and the resulting solution was then cooled with ice. After addition of 26.0 g of p-toluenesulfonyl chloride to the solution, the resulting mixture was stirred for 6 hours at room temperature. Ether was added to the resulting reaction mixture, and the mixture was then washed with water and dried over magnesium sulfate. Subsequently, the solvent was distilled out under reduced pressure to obtain a tosylated compound.

To the obtained tosylated compound were added 17.0 of methyl- p-hydroxybenzoate and 7.4 g of potassium hydroxide, and the mixture was then refluxed in 50 ml of methanol for 14 hours. After addition of an aqueous potassium hydroxide solution containing 18.0 g of potassium hydroxide, the resulting mixture was further refluxed for 5 hours. After addition of 1 l of water, hydrochloric acid was added dropwise to the mixture to lower the value of pH to 2. the generated precipitate was collected and dried by heating, to obtain 13.3 g of added 10 μl of stannic chloride. Polymerization reaction was carried out for 30 hours at room temperature. After the conclusion of the reaction, the reaction solution was concentrated and purified by column chromatography to obtain 0.6 g of the objective polymer having the repeating unit represented by the following formula. (Yield: 84%)

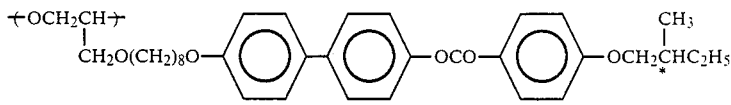

the objective carboxylic acid compound. (Yield: 56%).

8.(3) Synthesis of 4″-(8-allyloxyoctyloxy)biphenyl-4′-yl 4-(2-methylbutyloxy)benzoate To 2.4 g of the carboxylic acid compound obtained in 8.(2) was added 8.0 g of thionyl chloride, and the mixture was then heated at 80° C. for 3 hours with stirring. After the conclusion of the reaction, the excessive thionyl chloride was distilled out under reduced pressure to obtain an acid chloride compound.

Figure 16:
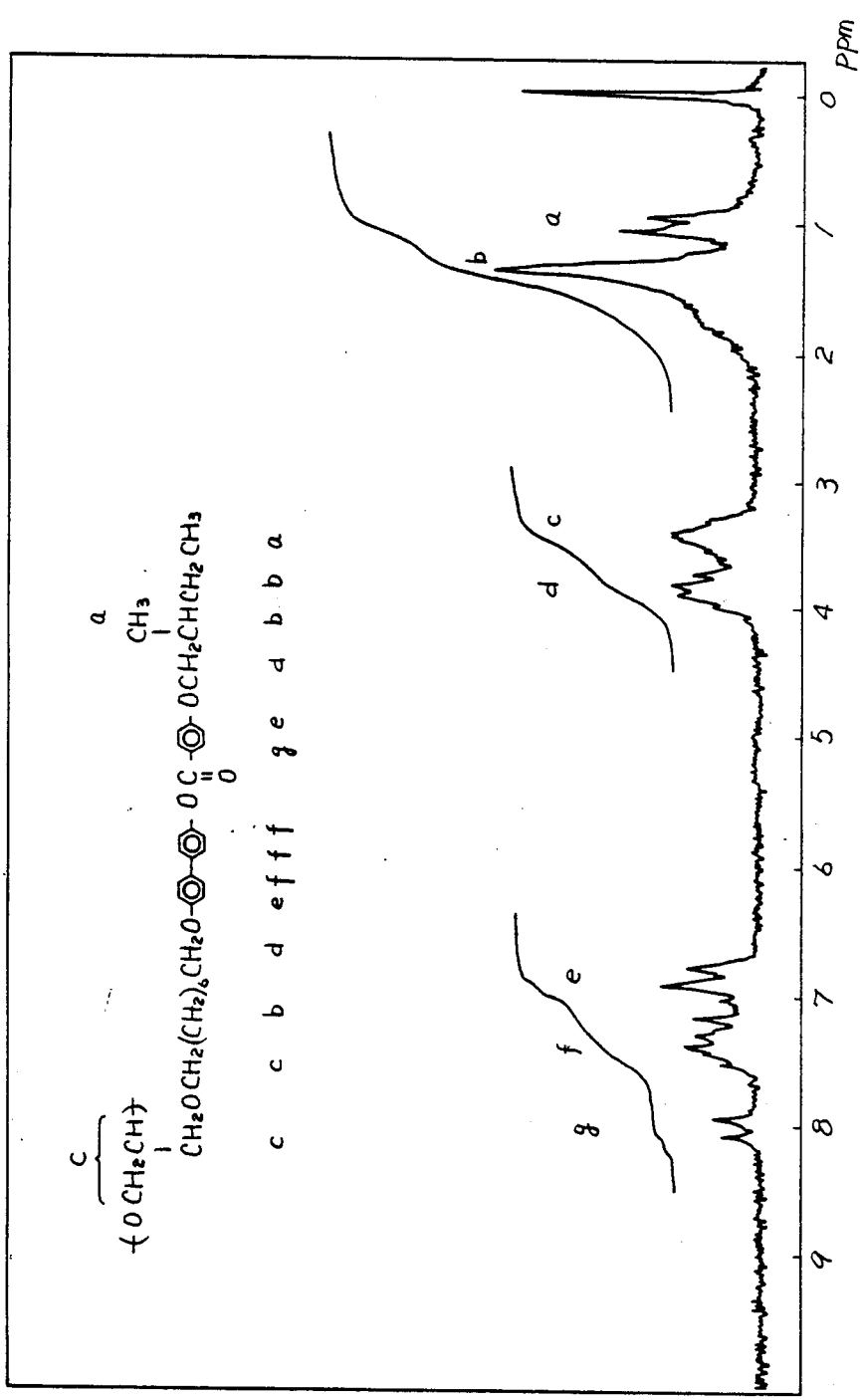
FIG. 16 is a chart of NMR spectrum of the ferroelectric liquid-crystalline polymer obtained in Example 8.

The chart of NMR spectrum of the obtained polymer and each hydrogen being attributed to for each peak in the chart are shown in FIG. 16, and the number average molecular weight, phase transition behavior, spontaneous polarization intensity, and electric field response time of the polymer are shown in Table 2.

EXAMPLE 9

Synthesis of Monomer

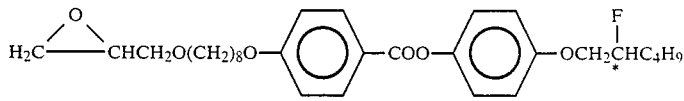

A THF solution of the acid chloride compound obtained above was added dropwise to a THF solution containing 4.0 g of the phenol compound obtained in 8.(1) and 1.3 g of triethylamine, and the resulting mixture was then stirred for one day at room temperature. After addition of ether, the resulting reaction mixture was washed with water and dried over magnesium sulfate, and the solvent was then distilled out under reduced pressure. The residue was recrystallized from methanol to obtain 5.0 g of the objective ester compound. (Yield: 80%).

8.(4) Conversion to epoxide 1.2 g of the ester compound obtained in 8.(3) was dissolved in dichloromethane, and the atmosphere of the system was replaced with argon. After addition of 0.5 g of m-chloroperbenzoic acid, the resulting mixture was stirred for 7 hours at room temperature. After the conclusion of the reaction, the reaction solution was washed with an aqueous potassium carbonate solution. After drying the reaction solution over magnesium sulfate, the solvent was distilled out under reduced pressure, to obtain 1.0 g of the objective monomer that is the epoxide represented by the above structural formula. (Yield: 81%).

Figure 15:
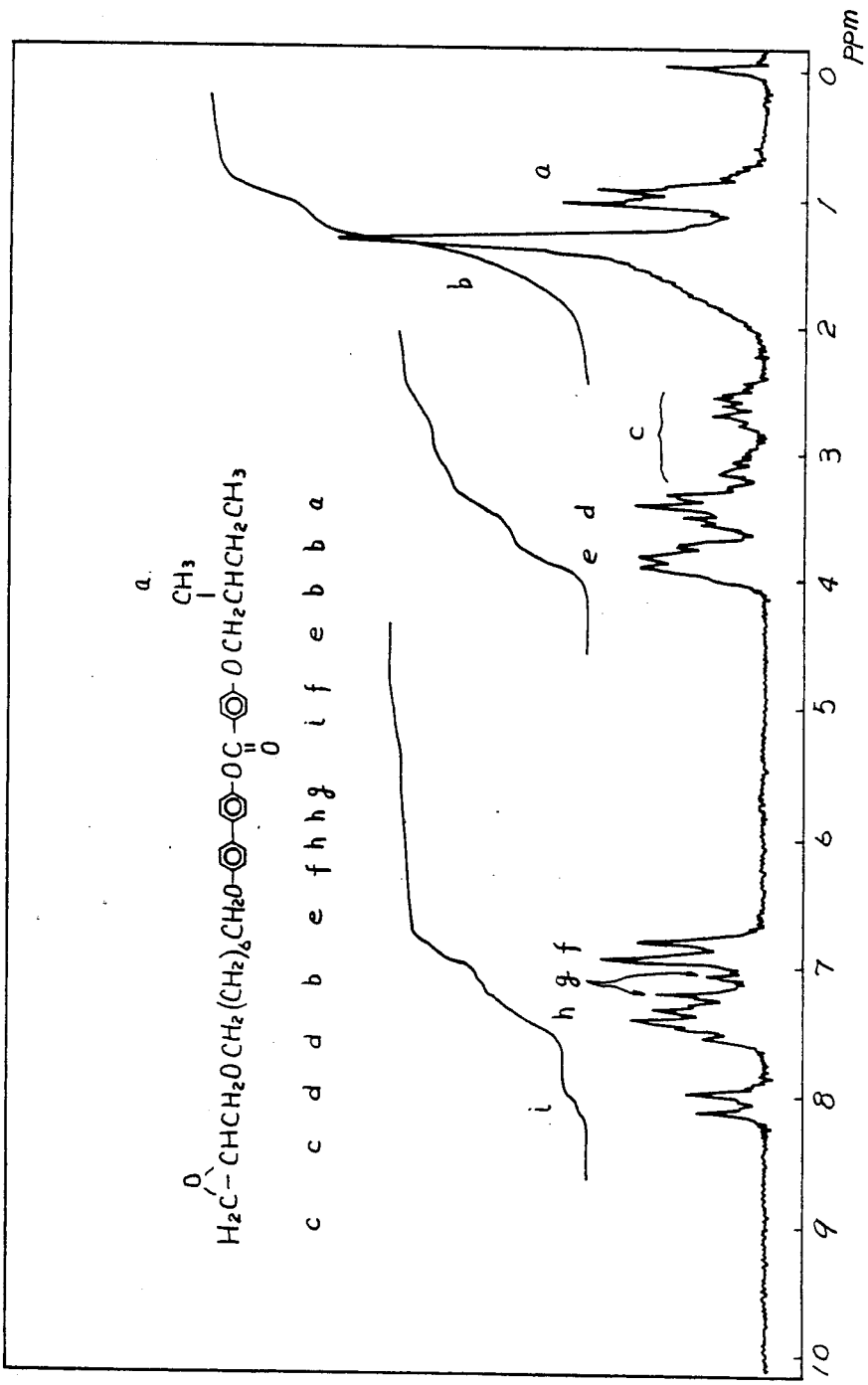
FIG. 15 is a chart of NMR spectrum of the epoxide obtained in Example 8.

The chart of NMR spectrum of the epoxide and each hydrogen being attributed to for each peak in the chart are shown in FIG. 15, and the result of elementary analysis is shown below.

|  | Elementary analysis values | |
| --- | --- | --- |
|  | C (%) | H (%) |
| Calculated values | 74.97 | 7.91 |
| Measured values | 75.0 | 7.9 |

Polymerization 1.0 g of the monomer obtained in 8.(4) was dissolved in dichloromethane, and the atmosphere of the system was replaced with argon. To the solution was then 9.(1) Synthesis of 4-(2-fluorohexyloxy)phenol 6.0 g of 2-fluorohexanol was dissolved in pyridine. To the resulting solution was added 10.0 g of p-toluenesulfonyl chloride, and the resulting mixture was then stirred for 10 hours at room temperature. After addition of ether, the mixture was washed with water and dried over magnesium sulfate, and the solvent was then distilled out under reduced pressure to obtain a tosylated compound.

To the tosylated compound obtained above were added 16.5 g of hydroquinone and 10.0 g of potassium hydroxiode, and the resulting mixture was refluxed in methanol for 16 hours in an atmosphere of argon. After addition of hydrochloric acid, the insoluble matters were removed away by filtration, and the solvent was then distilled out under reduced pressure from the resulting solution. The residue was purified by column chromatography to obtain 7.6 g of the objective phenol compound. (Yield: 72%).

9.(2) Synthesis of 4′-(2-fluorohexyloxy)phenyl 4-(8-allyloxyoctyloxy)benzoate

A mixture of 3.3 g of 4-(8-allyloxyoctyloxy)benzoic acid, three drops of pyridine, and 8 g of thionyl chloride was heated at 80° C. and 3 hours with stirring. After the conclusion of the reaction, the excessive thionyl chloride was distilled out under reduced pressure to obtain an acid chloride compound.

A toluene solution of the acid chloride compound obtained above was added dropwise to a toluene solution containing 1.9 g of the phenol compound obtained in 9.(1) and 1.2 g off triethylamine, and the mixture was then stirred for 8 hours at room temperature. Subsequently, the mixture was washed with water and dried over magnesium sulfate, and the solvent was then distilled out under reduced pressure. The residue was purified by column chromatography to obtain 2.7 g of the objective ester compound. (Yield. 60%).

9.(3) Conversion to Epoxide 2.7 g of the ester compound obtained in 9 (2) was dissolved in dichloromethane, and the atmosphere of the system was replaced with nitrogen. After addition of 1.2 g of m-chloroperbenzoic acid, the mixture was stirred for 7 hours at room temperature. After the conclusion of the reaction, the reaction solution was washed with an aqueous potassium carbonate solution. After drying the reaction solution over magnesium sulfate, the solvent was distilled out under reduced pressure, to obtain 2.4 g of the objective monomer that is the epoxide represented by the above structural formula. (Yield: 86%).

Figure 17:
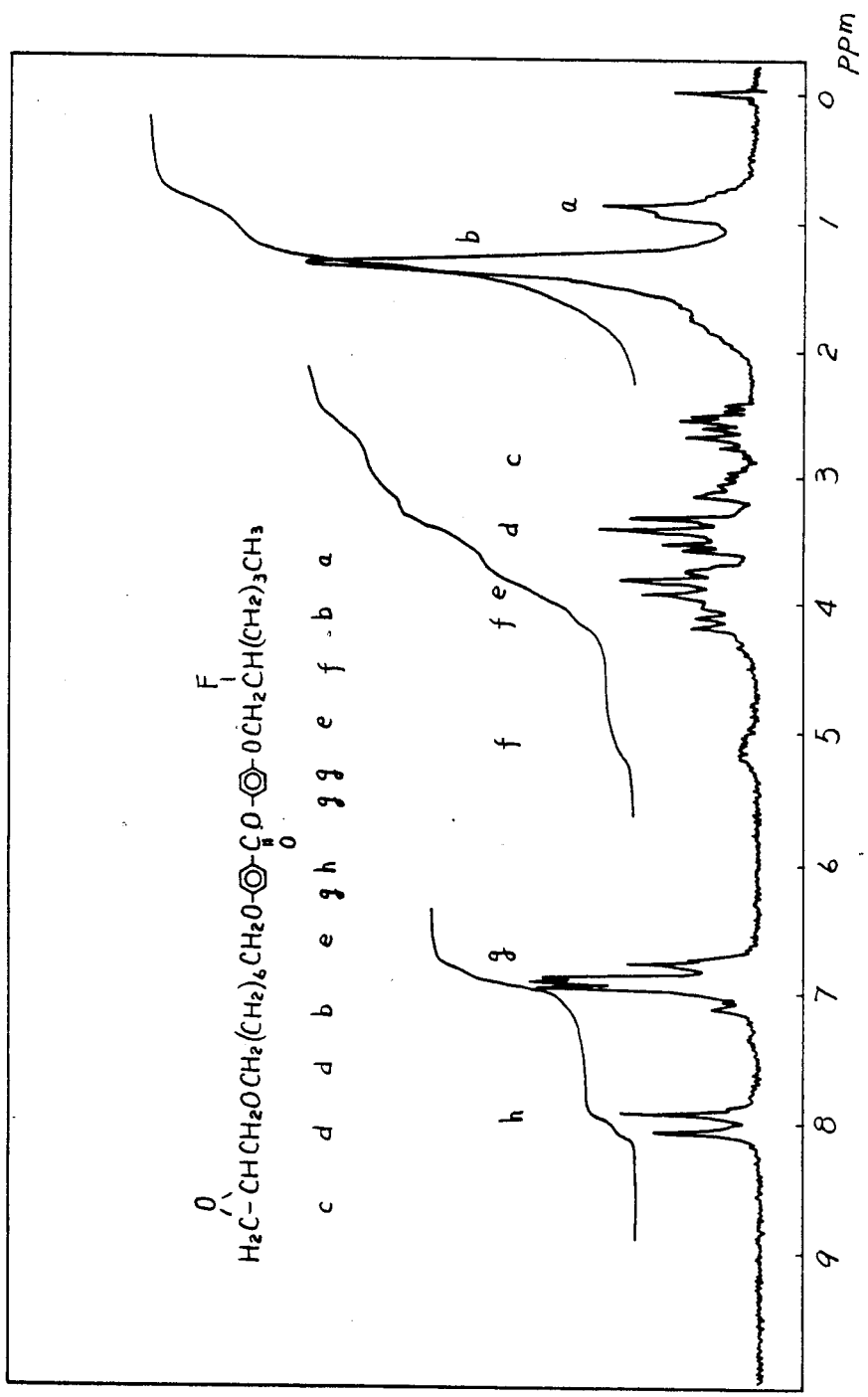
FIG. 17 is a chart of NMR spectrum of the epoxide obtained in Example 9.

The chart of NMR spectrum of the epoxide and each hydrogen being attributed to for each peak in the chart are shown in FIG. 17, and the result of elementary analysis is shown below.

|  | Elementary analysis values | | |
| --- | --- | --- | --- |
|  | C (%) | H (%) | F (%) |
| Calculated values | 69.74 | 8.00 | 3.68 |
| Measured values | 69.8 | 7.9 | 3.6 |

Polymerization 2.0 g of the monomer obtained in 9.(3) was dissolved in dichloromethane, and the atmosphere of the system was replaced with nitrogen. To the solution was then added 23 μl of stannic chloride. Polymerization reaction was carried out for 30 hours at room temperature. After the conclusion of the reaction, the reaction solution was concentrated and purified by column chromatography to obtain 1.8 g of the objective polymer having the repeating unit represented by the following formula. (Yield: 90%).

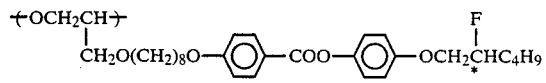

Figure 18:
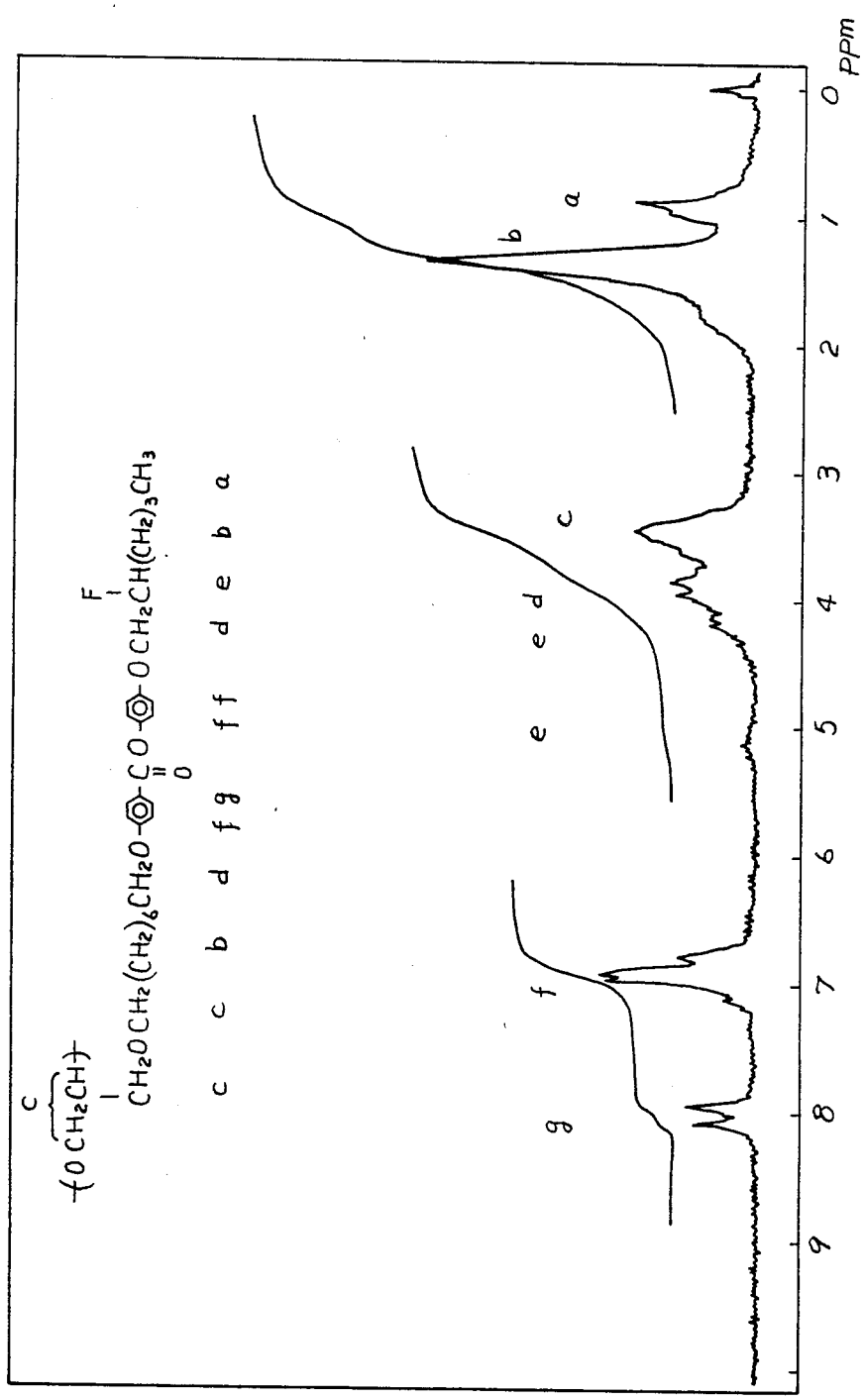
FIG. 18 is a chart of NMR spectrum of the ferroelectric liquid-crystalline polymer obtained in Example 9.

The chart of NMR spectrum of the obtained polymer and each hydrogen being attributed to for each peak in the chart are shown in FIG. 18, and the number average molecular weight, phase transition behavior, spontaneous polarization intensity, and electric field response time of the polymer are shown in Table 2.

Synthesis of Monomer

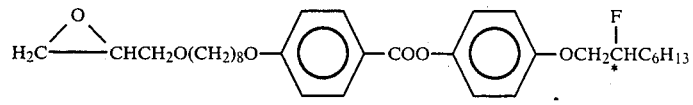

10.(1) Synthesis of 4-(2-fluorooctyloxy)phenol 7.4 g of 2-fluorooctanol was dissolved in pyridine. To the resulting solution was added 10.0 g of p-toluenesulfonyl chloride, and the resulting mixture was stirred for 10 hours at room temperature. After addition of ether, the resulting solution was washed with water and dried over magnesium sulfate, and the solvent was then distilled out under reduced pressure to obtain a tosylated compound.

A mixture of the tosylated compound obtained above, 16.5 g of hydroquinone, and 10.0 g of potassium hydroxide was refluxed in methanol for 16 hours in an atmosphere of argon. After addition of hydrochloric acid, the insoluble matters were removed away by filtration, and the solvent was distilled out from the solution under reduced pressure. The residue was purified by column chromatography to obtain 6.5 g of the objective phenol compound. (Yield: 54%).

10.(2) Synthesis of 4'-(2-fluorooctyloxy)phenyl 4-(8-allyloxyoctyloxy)benzoate

A mixture of 5.5 g of 4-(8-allyloxyoctyloxy)benzoic acid, three drops of pyridine, and 7 g of thionyl chloride was heated for 3 hours at 80° C. with stirring. After the conclusion of the reaction, the excessive thionyl chloride was distilled out under reduced pressure to obtain an acid chloride compound.

A toluene solution of the acid chloride compound obtained above was added dropwise to a toluene solution containing 3.0 g of the phenol compound obtained in 10.(1) and 2.0 g of triethylamine, and the mixture was then stirred for 8 hours at room temperature. The reaction mixture was then washed with water and dried over magnesium sulfate, and the solvent was then distilled out under reduced pressure. The residue was purified by column chromatography to obtain 3.4 g of the objective ester compound. (Yield: 51%).

10.(3) Conversion to epoxide 3.4 g of the ester compound obtained in 10.(2) was dissolved in dichloromethane, and the atmosphere of the system was replaced with nitrogen. After addition of 1.6 g of m-chloroperbenzoic acid, the resulting mixture was then stirred for 7 hours at room temperature. After the conclusion of the reaction, the reaction solution was washed with an aqueous potassium carbonate solution. After drying the reaction solution over magnesium sulfate, the solvent was then distilled out under reduced pressure, to obtain 3.0 g of the objective monomer that is the epoxide represented by the above structural formula. (Yield: 86%).

Figure 19:
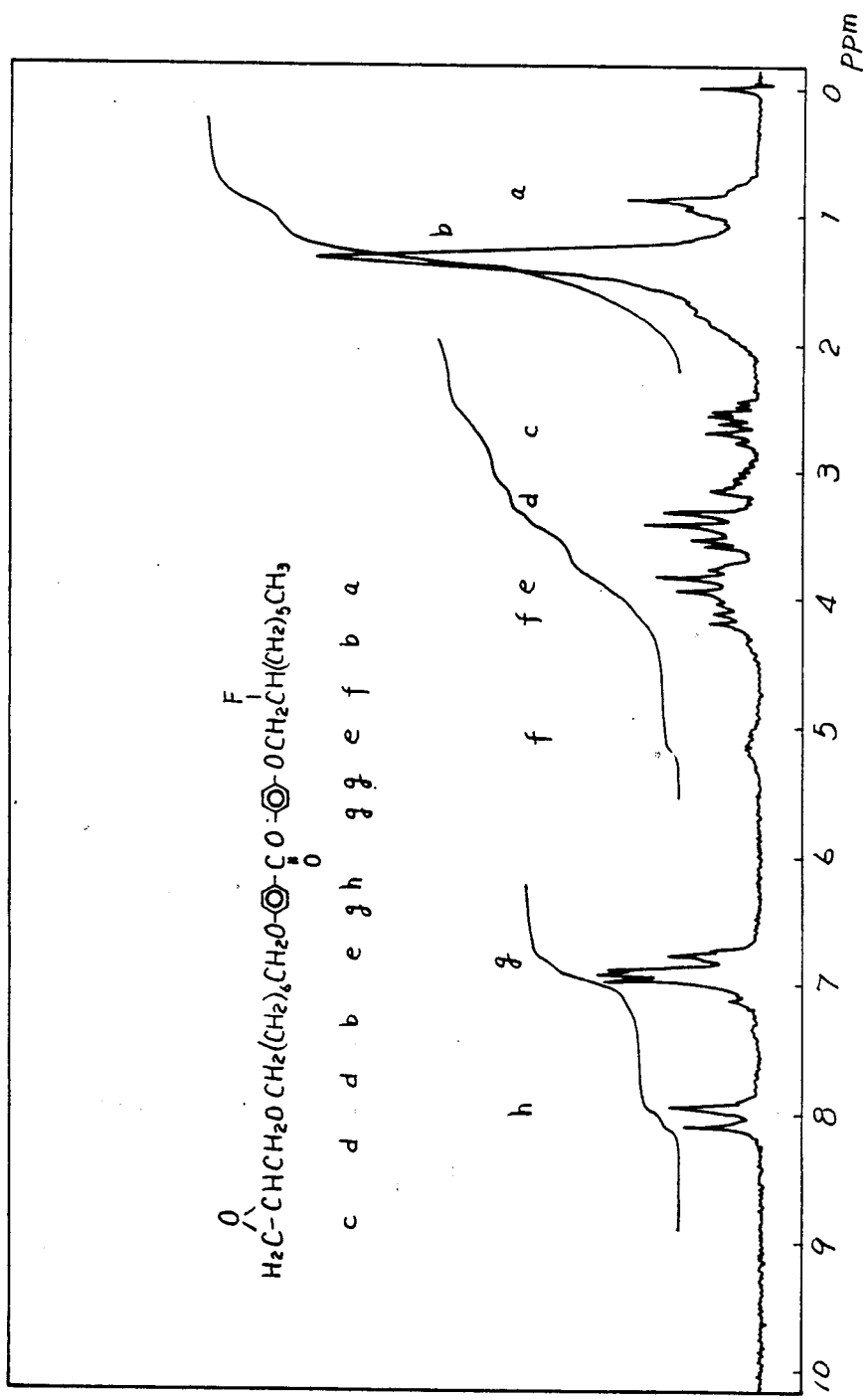
FIG. 19 is a chart of NMR spectrum of the epoxide obtained in Example 10.

The chart of NMR spectrum of the epoxide and each hydrogen being attributed to for each peak in the chart are shown in FIG. 19, and the result of elementary analysis is shown below.

|  | Elementary analysis values | | |
| --- | --- | --- | --- |
|  | C (%) | H (%) | F (%) |
| Calculated values | 70.56 | 8.33 | 3.49 |
| Measured values | 70.7 | 8.2 | 3.4 |

Polymerization 3.0 g of the monomer obtained in 10.(3) was dissolved in dichloromethane, and the atmosphere of the system was replaced with nitrogen. To the solution was then added 30 μl of stannic chloride. Polymerization reaction was carried out for 30 hours at room temperature. After the conclusion of the reaction, the reaction solution was concentrated and purified by column chromatography to obtain 1.9 g of the objective polymer having the repeating unit represented by the following formula. (Yield: 63%).

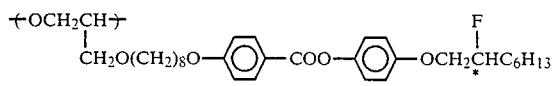

Figure 20:
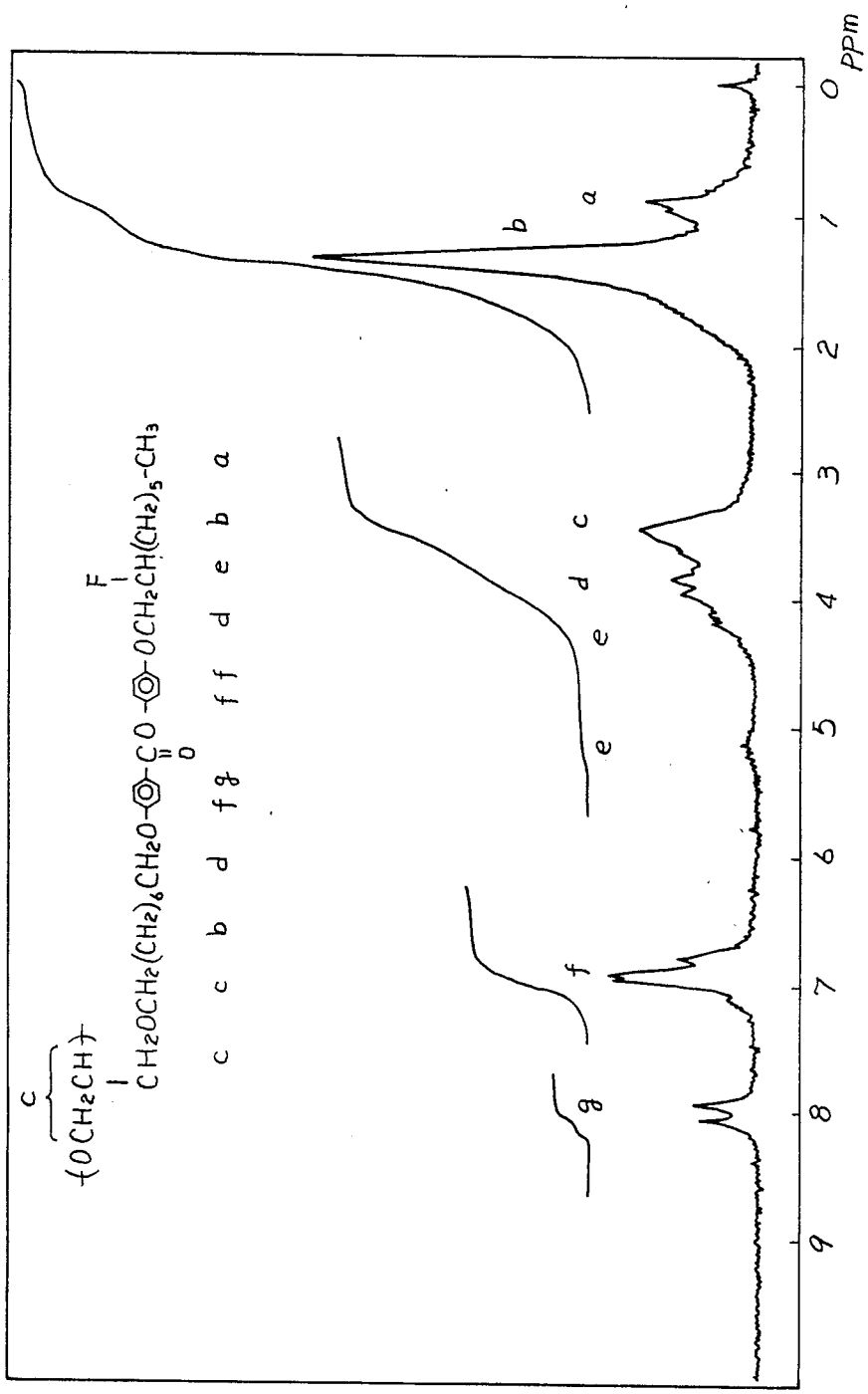
FIG. 20 is a chart of NMR spectrum of the ferroelectric liquid-crystalline polymer obtained in Example 10.

The chart of NMR spectrum of the obtained polymer and each hydrogen being attributed to for each peak in the chart are shown in FIG. 20, and the number average molecular weight, phase transition behavior, spontaneous polarization intensity, and electric field response time of the polymer are shown in Table 2.

EXAMPLE 11

Synthesis of Monomer

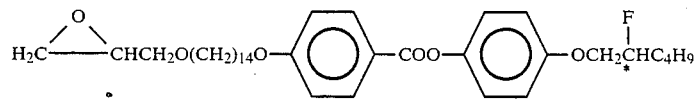

11.(1) Synthesis of 14-bromotetradecyl allyl ether

The procedure in 4.(1) in Example 4 was repeated with the exception that 2.0 g off allyl alcohol, 1.7 g of 60% sodium hydride, and 30 g of 1,14-dibromotetradecane were used, to obtain 7.9 g of the objective ω-haloalkyl allyl ether. (Yield: 69%).

11.(2) Synthesis of 4-(14-allyloxytetradecyloxy)benzoic acid

The reaction and procedure in 1.(2) in Example 1 were repeated with the exception that 7.9 g of the allyl ether compound obtained in 11.(1), 3.6 g of methyl p-hydroxybenzoate, and 1.6 g of potassium hydroxide were used, to obtain 6.8 g of the objective carboxylic acid compound. (Yield: 74%).

11.(3) Synthesis of 4'(2-fluorohexyloxy)phenyl 4-(14-allyloxytetradecyloxy)benzoate A mixture of 3.9 g of 4-(14-allyloxytetradecyloxy)-benzoate acid, three drops of pyridine, and 5.0 g of thionyl chloride was heated at 80° C. for 3 hours with stirring. After the conclusion of the reaction, the excessive thionyl chloride was distilled out under reduced pressure to obtain an acid chloride compound.

A toluene solution of the acid chloride compound obtained above was added dropwise to a toluene solution containing 2.4 g of 4-(2-fluorohexyloxy)phenol and 1.1 g of triethylamine, and the resulting mixture was stirred for 8 hours at room temperature. After the reaction mixture was washed with water and dried over magnesium sulfate, the solvent was then distilled out under reduced pressure. The residue was purified by column chromatography to obtain 3.5 g of the objective ester compound. (Yield: 58%).

11.(4) Conversion to epoxide 3.5 g of the ester compound obtained in 11.(3) was dissolved in dichloromethane, and the atmosphere of the system was replaced with nitrogen. After addition of 1.2 g of m-chloroperbenzoic acid, the resulting mixture was stirred for 7 hours at room temperature. After the conclusion of the reaction, the reaction solution was washed with an aqueous potassium carbonate solution. After drying the reaction solution over magnesium sulfate, the solvent was then distilled out under reduced pressure, to obtain 3.4 g of the objective monomer that is the epoxide represented by the above structural formula. (Yield: 95%).

Figure 21:
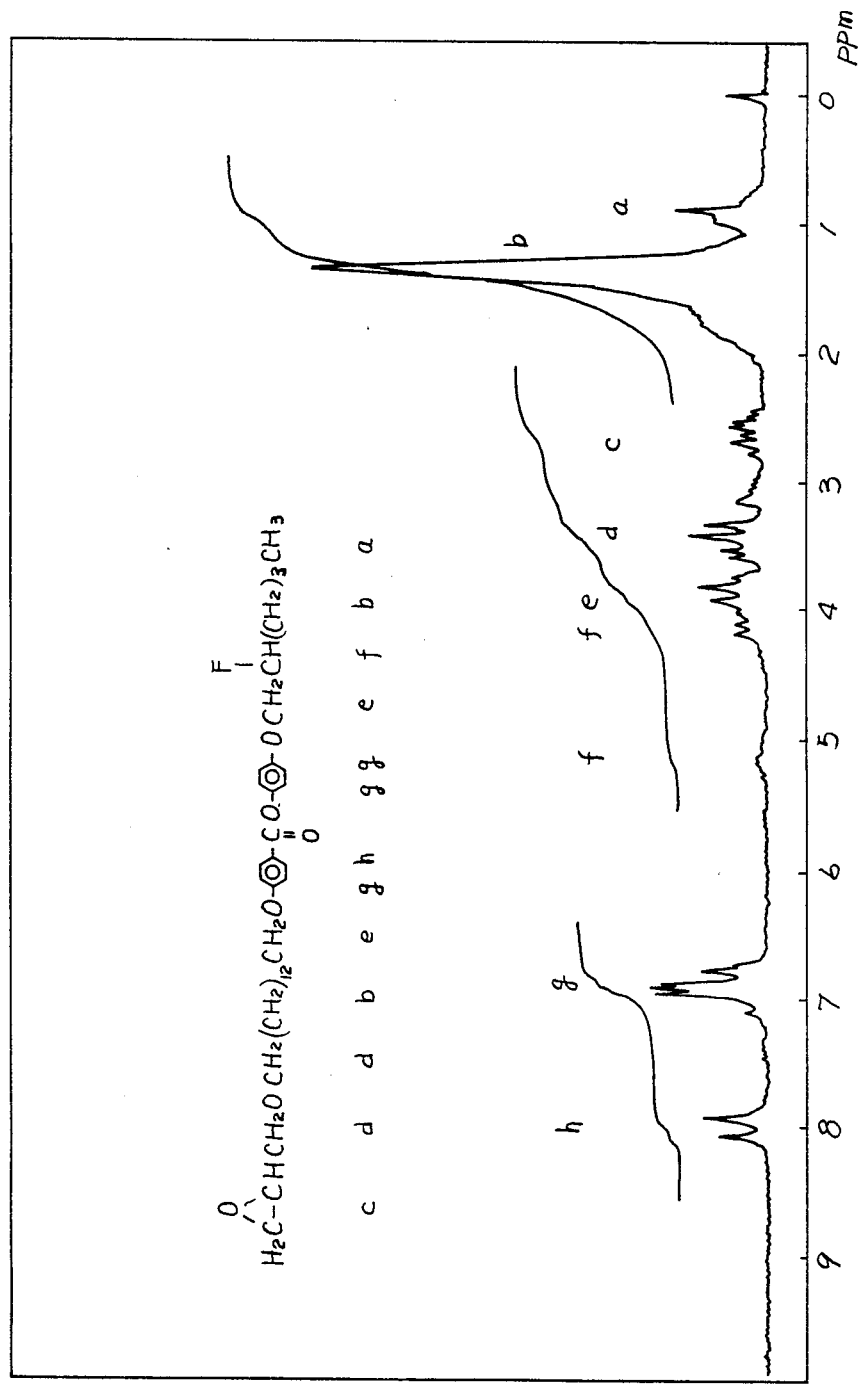
FIG. 21 is a chart of NMR spectrum of the epoxide obtained in Example 11.

The chart of NMR spectrum of the epoxide and each hydrogen being attributed to for each peak in the chart are shown in FIG. 21, and the result of elementary analysis is shown below.

|  | Elementary analysis values | | |
| --- | --- | --- | --- |
|  | C (%) | H (%) | F (%) |
| Calculated values | 73.97 | 8.89 | 3.16 |
| Measured values | 74.0 | 8.9 | 3.0 |

Polymerization 3.4 g of the monomer obtained in 11.(4) was dissolved in dichloromethane, and the atmosphere of the system was replaced with nitrogen. To the solution was then added 30 μl of stannic chloride. Polymerization reaction was carried out for 30 hours at room temperature. After the conclusion of the reaction, the reaction solution was concentrated and purified by column chromatography to obtain 1.8 g of the objective polymer having the repeating unit represented by the following formula. (Yield: 54%).

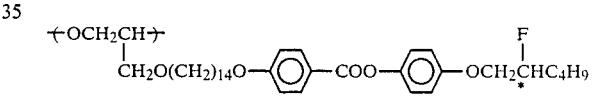

Figure 22:
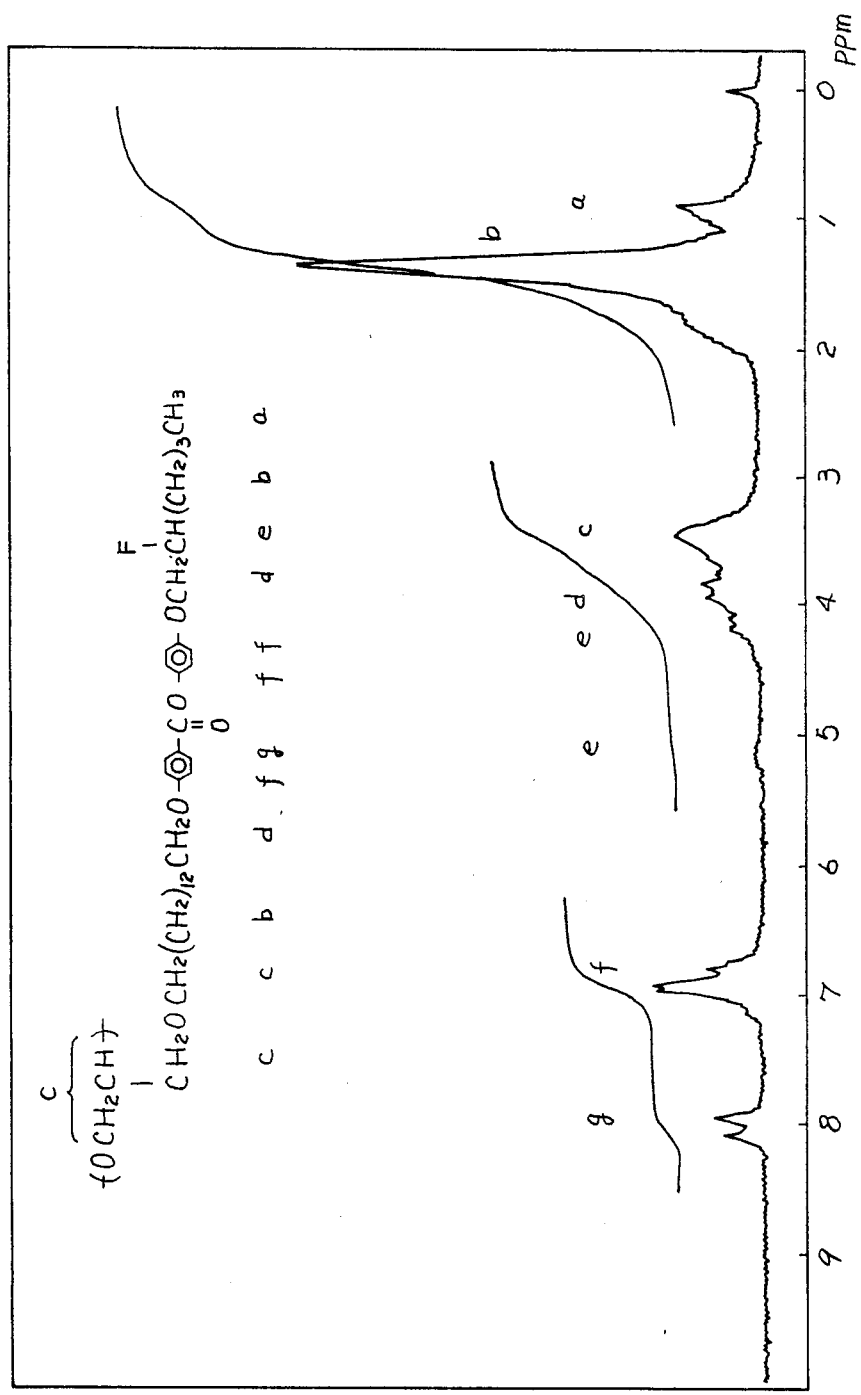
FIG. 22 is a chart of NMR spectrum of the ferroelectric liquid-crystalline polymer obtained in Example 11.

The chart of NHMR spectrum of the obtained polymer and each hydrogen being attributed to for each peak in the chart are shown in FIG. 22, and the number average molecular weight, phase transition behavior, spontaneous polarization intensity, and electric field response time of the polymer are shown in Table 2.

EXAMPLE 12

Synthesis of Monomer 2.0 g of the monomer synthesized in Example 1 and 3.6 g of the monomer synthesized in Example 6 were dissolved in dichloroethane, and the atmosphere of the system was then replaced with argon. After addition of boron trifluoride (1 mol % of the sum of the monomers), polymerization reaction was carried out for 8 hours at room temperature. After conclusion of the reaction, the reaction solution was concentrated, and the resulting concentrate was purified by column chromatography to obtain 4.2 g of the objective copolymer having the repeating units represented by the following formulas. (Yield: 75%).

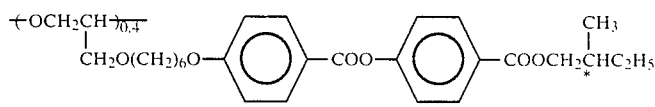

Figure 23:
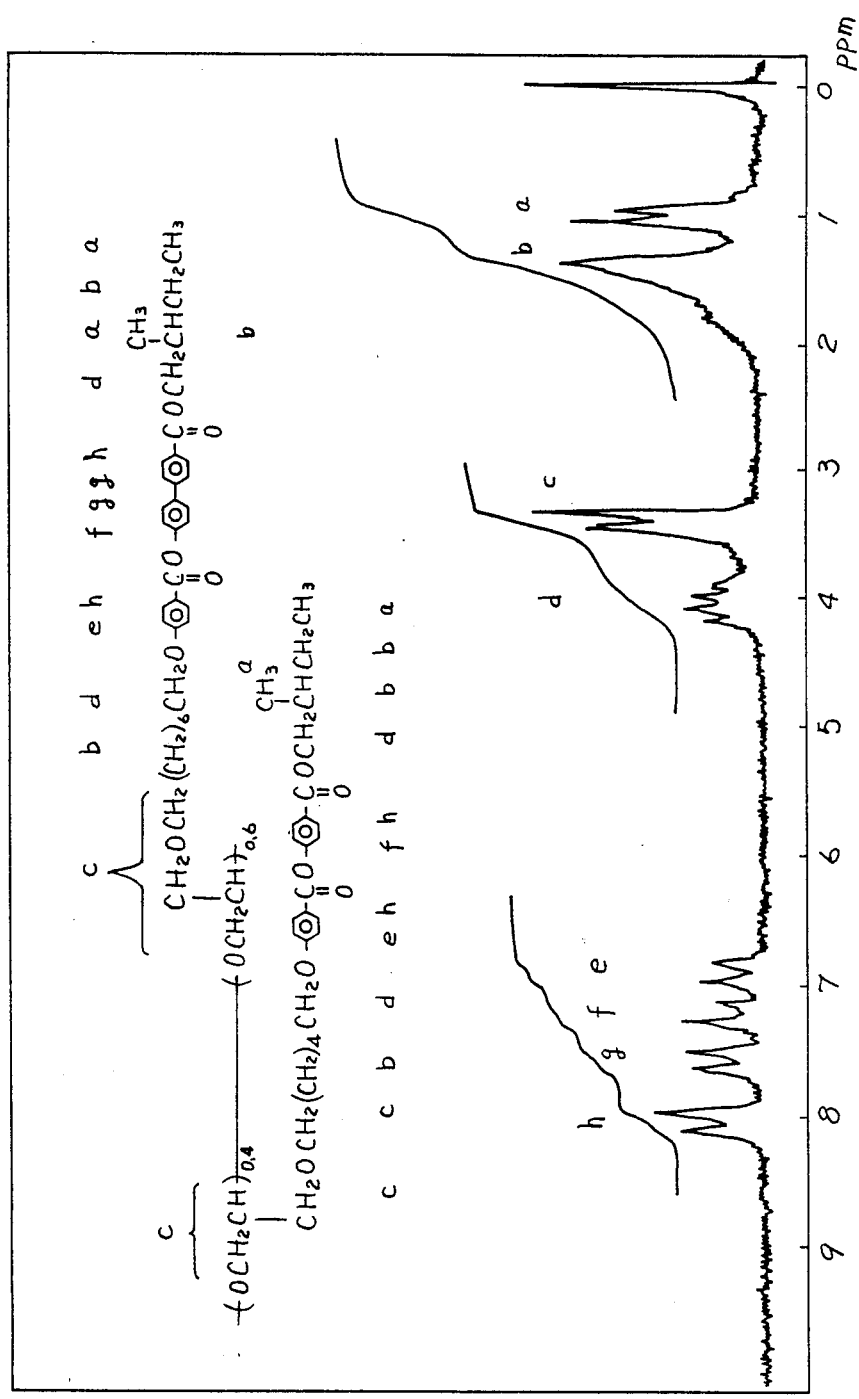
FIG. 23 is a chart of NMR spectrum of the ferroelectric liquid-crystalline polymer obtained in Example 12.

-continued
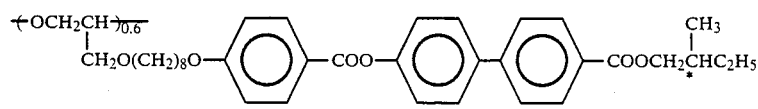
The chart of NMR spectrum of the obtained polymer and each hydrogen being attributed to for each peak in the chart shown in FIG. 23, and the number average molecular weight, phase transition behavior, spontaneous polarization intensity, and electric field response time of the polymer are shown in Table 2.

TABLE 1

| Example No. | Repeating unit | Number average molecular weight | Phase transition behavior (°C.) | Spontaneous polarization intensity ($10^{-5}$ C · m$^{-2}$) (Measuring temperature (°C.)) | Electric field response speed (ms) (Measuring temperature (°C.)) |
|---|---|---|---|---|---|
| 1 | $\text{+OCH}_2\text{CH+}$ / $\text{CH}_2\text{O(CH}_2\text{)}_6\text{O}-\bigcirc-\text{COO}-\bigcirc-\text{COOCH}_2\overset{*}{\text{C}}\text{HC}_2\text{H}_5$ with CH$_3$ | 1,600 | glass $\xrightarrow{-39}_{-40}$ S $\xrightarrow{-9}_{-9}$ SmC* $\xrightarrow{11.5}_{9}$ SmA $\xrightarrow{28}_{24}$ Iso | 10 (−5) | 15 (5) |
| 2 | $\text{+OCH}_2\text{CH+}$ / $\text{CH}_2\text{O(CH}_2\text{)}_6\text{O}-\bigcirc-\bigcirc-\text{COOCH}_2\overset{*}{\text{C}}\text{HC}_2\text{H}_5$ with CH$_3$ | 2,000 | glass $\xrightarrow{-27}_{-30}$ S $\xrightarrow{9}_{-3}$ SmC* $\xrightarrow{42}_{42}$ SmA $\xrightarrow{62}_{52.5}$ Iso | 8 (20) | 8 (30) |
| 3 | $\text{+OCH}_2\text{CH+}$ / $\text{CH}_2\text{O(CH}_2\text{)}_6\text{O}-\bigcirc-\text{COO}-\bigcirc-\text{COOCH}_2\overset{*}{\text{C}}\text{HC}_6\text{H}_{13}$ with F | 2,200 | glass $\xrightarrow{30}$ S $\xleftarrow{-25}$ SmC* $\xrightarrow{0}$ SmC* $\xrightarrow{25}$ SmA $\xrightarrow{38}_{36}$ N $\xrightarrow{40}_{39.5}$ Iso | 43 (20) | 5 (20) |
| 4 | $\text{+OCH}_2\text{CH+}$ / $\text{CH}_2\text{O(CH}_2\text{)}_8\text{O}-\bigcirc-\bigcirc-\text{COOCH}_2\overset{*}{\text{C}}\text{HC}_4\text{H}_9$ with F | 3,000 | glass $\xrightarrow{-32}_{-35}$ S $\xrightarrow{6}_{-10}$ SmC* $\xrightarrow{39}_{39}$ SmA $\xrightarrow{62}_{57}$ Iso | 120 (20) | 4 (30) |
| 5 | $\text{+OCH}_2\text{CH+}$ / $\text{CH}_2\text{O(CH}_2\text{)}_8\text{O}-\bigcirc-\text{COO}-\bigcirc-\text{OCOCH}-\overset{*}{\text{C}}\text{HC}_2\text{H}_5$ with Cl, CH$_3$ | 2,300 | glass $\xrightarrow{-20}_{-25}$ S $\xrightarrow{22}_{15}$ SmC* $\xrightarrow{60}_{60}$ SmA $\xrightarrow{80}_{70}$ Iso | 71 (30) | 5 (45) | glass: glass state
S: an unidentified smectic phase
SmC*: chiral smectic C phase
SmA: smectic A phase
N: nematic phase
Iso: isotropic phase

TABLE 2

| Example No. | Repeating unit | Number average molecular weight | Phase transition behavior (°C.) | Spontaneous polarization intensity ($10^{-5}$ C·m$^{-2}$) (Measuring temperature (°C.)) | Electric field response speed (ms) (Measuring temperature (°C.)) |
|---|---|---|---|---|---|
| 6 | $+OCH_2CH+$ / $CH_2O(CH_2)_8O-$〇-COO-〇-〇-COOCH$_2$*CHC$_2$H$_5$ / CH$_3$ | 3,300 | glass $\overset{-20}{\underset{-24}{\rightleftarrows}}$ S $\overset{-10}{\underset{-10}{\rightleftarrows}}$ SmC* $\overset{110}{\underset{109}{\rightleftarrows}}$ SmA $\overset{142}{\underset{142}{\rightleftarrows}}$ Iso | 6 (60) | 1 (60) 15 (30) |
| 7 | $+OCH_2CH+$ / $CH_2O(CH_2)_{10}O-$〇-COO-〇-〇-COOCH$_2$*CHC$_3$H$_7$ / CH$_3$ | 4,100 | glass $\overset{-25}{\underset{-25}{\rightleftarrows}}$ S $\overset{15}{\underset{10}{\rightleftarrows}}$ SmC* $\overset{150}{\underset{149}{\rightleftarrows}}$ SmA $\overset{183}{\underset{182}{\rightleftarrows}}$ Iso | 100 (75) | 1 (75) 20 (50) |
| 8 | $+OCH_2CH+$ / $CH_2O(CH_2)_8O-$〇-OCO-〇-〇-OCH$_2$*CHC$_2$H$_5$ / CH$_3$ | 3,500 | glass $\overset{80}{\underset{79}{\rightleftarrows}}$ SmC* $\overset{100}{\underset{98}{\rightleftarrows}}$ SmA $\overset{105}{\underset{102}{\rightleftarrows}}$ Ch $\overset{135}{\underset{129}{\rightleftarrows}}$ Iso | 5 (85) | 3 (85) |
| 9 | $+OCH_2CH+$ / $CH_2O(CH_2)_8O-$〇-COO-〇-〇-OCH$_2$*CHC$_4$H$_9$ / F | 2,100 | glass $\overset{25}{\underset{25}{\rightleftarrows}}$ SmC* $\overset{59}{\underset{55}{\rightleftarrows}}$ SmA $\overset{75}{\underset{74}{\rightleftarrows}}$ Iso | 150 (30) | 2 (30) |
| 10 | $+OCH_2CH+$ / $CH_2O(CH_2)_8O-$〇-COO-〇-〇-OCH$_2$*CHC$_6$H$_{13}$ / F | 2,100 | glass $\overset{25}{\underset{25}{\rightleftarrows}}$ SmC* $\overset{70}{\underset{67}{\rightleftarrows}}$ SmA $\overset{89}{\underset{85}{\rightleftarrows}}$ Iso | 120 (30) | 2 (30) |
| 11 | $+OCH_2CH+$ / $CH_2O(CH_2)_{14}O-$〇-COO-〇-〇-OCH$_2$*CHC$_4$H$_9$ / F | 2,400 | Cry $\overset{19}{\underset{10}{\rightleftarrows}}$ SmC* $\overset{53}{\underset{49}{\rightleftarrows}}$ SmA $\overset{84}{\underset{82}{\rightleftarrows}}$ Iso | 140 (30) | 3 (30) |
| 12 | $+OCH_2CH+_{0.4}$ / $CH_2O(CH_2)_6O-$〇-COO-〇-〇-COOCH$_2$*CHC$_2$H$_5$ / CH$_3$ $+OCH_2CH+_{0.6}$ / $CH_2O(CH_2)_8O-$〇-COO-〇-〇-COOCH$_2$*CHC$_2$H$_5$ / CH$_3$ | 2,800 | glass $\overset{-15}{\underset{-18}{\rightleftarrows}}$ S $\overset{0}{\underset{0}{\rightleftarrows}}$ SmC* $\overset{74}{\underset{72}{\rightleftarrows}}$ SmA $\overset{103}{\underset{102}{\rightleftarrows}}$ Iso | 7 (30) | 5 (30) | glass: glass state
S: an unidentified smectic phase
SmC*: chiral smectic C phase
SmA: smectic A phase
Iso: isotropic phase
Ch: cholesteric phase

What is claimed is:

1. A ferroelectric liquid-crystalline polymer consisting essentially of at least one repeating unit represented by the following general formula:

wherein
k is an integer having a value of 2 to 30;
$R^1$ is

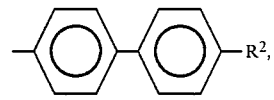

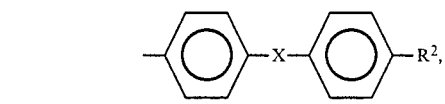

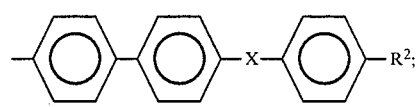

X is —COO— or —OCO—; and
$R^2$ is —COOR$^3$, —COOR$^3$ or —OR$^3$;
wherein
$R^3$ is

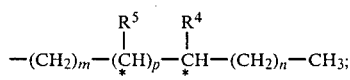

wherein
each of $R^4$ is independently —CH$_3$, a halogen atom or —CN;
each of m and n is independently an integer having a value of 0 to 10, with the proviso that when $R^4$ is —CH$_3$, n is not an integer having a value of 0;
p is an integer having a value of 0 or 1; and
C marked with * is an asymmetric carbon atom.

2. The ferroelectric liquid-crystalline polymer as claimed in claim 1, wherein k is an integer having a value of 4 to 20, m is an integer having a value of 0 to 6, and n is an integer having a value of 0 to 6.

3. The ferroelectric liquid-crystalline polymer as claimed in claim 1 or 2, wherein $R^1$ is

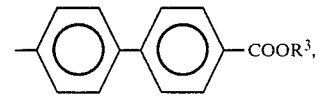

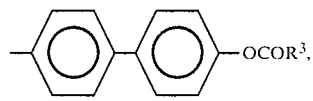

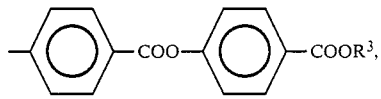

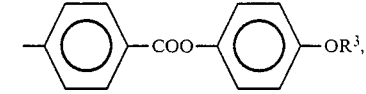

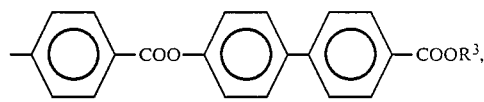

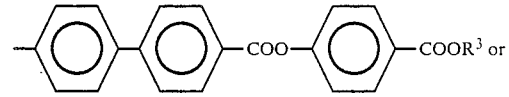

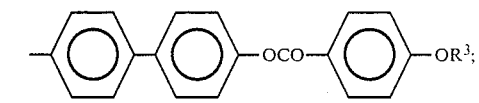

$R^3$ is

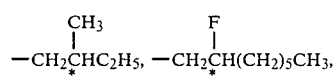

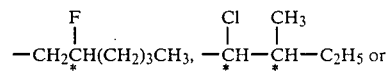

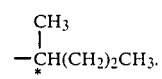

4. An epoxide having the structure represented by the following general formula:

wherein
k is an integer having a value of 2 to 30;
$R^1$ is

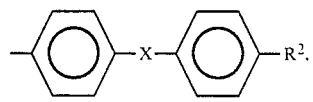

-continued

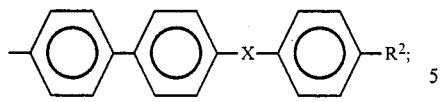

X is —COO— or —OCO—; and
R² is —COOR³, —OCOR³ or —OR³;
wherein
R³ is

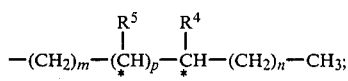

wherein
each of R⁴ and R⁵ is independently —CH₃, a halogen atom or —CN;
each of m and n is independently an integer having a value of 0 to 10, with the proviso that when R⁴ is —CH₃, n is not an integer having a value of 0;
p is an integer having a value of 0 or 1; and
C marked with * is an asymmetric carbon atom.

5. The epoxide as claimed in claim 4, wherein k is an integer having a value of 4 to 20, m is an integer having a value of 0 to 6, and n is an integer having a value of 0 to 6.

6. The epoxide as claimed in claim 4 or 5, wherein R¹ is

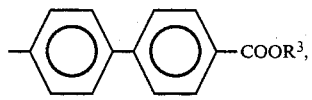

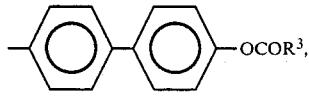

-continued

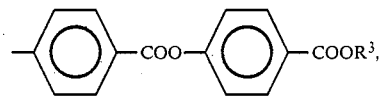

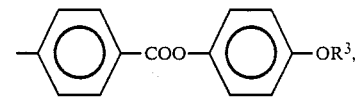

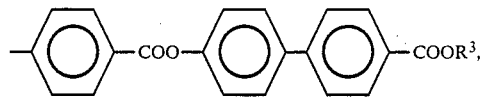

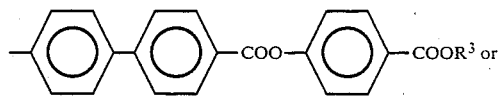

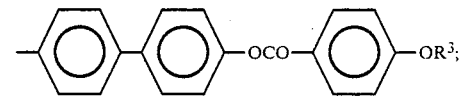

and
R³ is

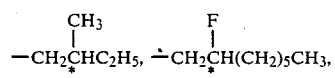

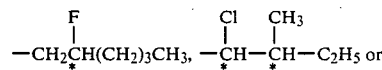

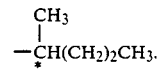

* * * * *